United States Patent
Kalindjian et al.

(10) Patent No.: US 6,878,734 B2
(45) Date of Patent: Apr. 12, 2005

(54) GASTRIN AND CHOLECYSTOKININ RECEPTOR LIGANDS(II)

(75) Inventors: Sarkis Barret Kalindjian, London (GB); Ildiko Maria Buck, London (GB); Katherine Isobel Mary Steel, London (GB); Paul Trevor Wright, London (GB); Matthew John Tozer, London (GB); Michael John Pether, London (GB); Caroline Minli Rachel Low, London (GB)

(73) Assignee: James Black Foundation Limited, London (GB)

( * ) Notice: Subject to any disclaimer, the term of this patent is extended or adjusted under 35 U.S.C. 154(b) by 0 days.

(21) Appl. No.: 10/275,741

(22) PCT Filed: May 4, 2001

(86) PCT No.: PCT/GB01/01964

§ 371 (c)(1),
(2), (4) Date: Apr. 7, 2003

(87) PCT Pub. No.: WO01/85723

PCT Pub. Date: Nov. 15, 2001

(65) Prior Publication Data

US 2003/0199565 A1 Oct. 23, 2003

(30) Foreign Application Priority Data

May 8, 2000 (GB) .............................. 0011089

(51) Int. Cl.[7] .................. A61K 31/415; C07D 405/04; C07D 413/02; C07D 237/08; C07D 247/02; C07D 233/06

(52) U.S. Cl. .................. 514/397; 548/125; 548/345.1; 548/364.1

(58) Field of Search ................ 548/125, 345.1–364.1; 514/397

(56) References Cited

FOREIGN PATENT DOCUMENTS

| EP | 0 454 449 | 4/1991 |
| EP | 0 712 847 | 5/1996 |
| WO | WO 91 00277 | 1/1991 |
| WO | WO 99 01435 | 1/1999 |

OTHER PUBLICATIONS

Huff et al., "The Preparation of Phenacylpyrazoles, . . . ", Juurnal of Heterocyclic Chemistry; vol. 22, No. 2, Mar. 1985, pp. 501–504.
Yousif et al., "Synthesis of 4–Substituted–3–Methyl–2–Phenylimidazoles", Croatica Chemica Acta, Croatian Chemical Society, vol. 60, No. 2, 1987, pp. 309–314.
Koskinen A., "13C NMR Spectroscopy of Substituted Imidazoles" Heterocycles, vol. 19, No. 9, 1982, pp. 1633–1635.
Vecchi et al., Reazioni Carbeniche Con Benzonitrilossido, La Chemica E L'Industria, vol. 58, No. 6, pp. 451.

Primary Examiner—Rita Desai
(74) Attorney, Agent, or Firm—Heller Ehrman White and McAuliffe LLP

(57) ABSTRACT

Ligands for the gastrin and cholecystokinin (CCK) receptors are provided, together with methods for preparing such ligands, and compounds which are useful intermediates in such methods. Pharmaceutical compositions comprising such ligands, methods for preparing such pharmaceutical compositions, and methods of treatment using these compositions also are provided. The ligands have the formula (I):

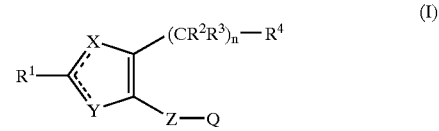

where n is from 1 to 3;
X and Y are independently =N— or —N($R^5$)— where $R^5$ is selected from the group consisting of H, Me, Et, Pr, Bn, —OH and —$CH_2COOR^6$, where $R^6$ represents H, Me, Et, Pr or Bn;
$R^1$ is H or a $C_1$–$C_{15}$ saturated carbocyclic ring optionally substituted with OMe, $NMe_2$, $CF_3$, Me, F, Cl, Br or I where up to three H atoms may optionally be replaced by halogen atoms;
$R^2$ is selected from H, Me, Et, Pr and OH, each $R^2$ being independently selected from H, Me, Et, Pr and OH when n is greater than 1;
$R^3$ is selected from the group consisting of H, Me, Et and Pr when n is 1; or, when n is greater than 1, each $R^3$ is independently selected from the group consisting of H, Me, Et and Pr, or two $R^3$ groups on neighbouring carbon atoms are linked to form a $C_3$ to $C_6$ carbocyclic ring, or two $R^3$ groups are absent from neighbouring carbon atoms which are linked by a double bond; or $R^2$ and $R^3$ on the same carbon atom together represent an =O group;
$R^4$ is H or a $C_3$ to $C_{10}$ alicyclic ring where up to three H atoms may optionally be replaced by halogen atoms;
Z is selected from the group consisting of:

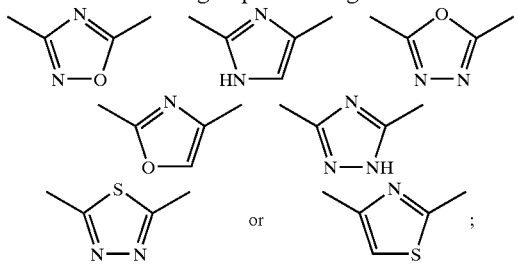

Q is a 6-membered aromatic carbocycle substituted with 1 or 2 V groups and optionally substituted with 1, 2 or 3 T groups;
V is selected from the group consisting of —CO—NH—$SO_2$—Ph, —$SO_2$—NH—CO—Ph, —$CH_2OH$, or a group of the formula —$R^7U$, where U is selected from the group consisting of —COOH, tetrazolyl, —CONHOH and —$SO_3H$; and $R^7$ is selected from the group consisting of a bond; $C_1$ to $C_6$ hydrocarbylene, optionally substituted by hydroxy, amino or acetamido; —O—($C_1$ to $C_3$ alkylene)-; —$SO_2NR^8$—$CHR^9$—; —CO—$NR^8$—$CHR^9$—, where $R^8$ and $R^9$ are independently selected from H and methyl; and —NH—(CO)$_c$—$CH_2$—, where c is 0 or 1.

14 Claims, No Drawings

GASTRIN AND CHOLECYSTOKININ RECEPTOR LIGANDS(II)

This application is the national phase under 35 U.S.C. §371 of PCT International Application No. PCT/GB01/01964 which has an International filing date of May 4, 2001, the disclosure of which is incorporated herein by reference in its entirety.

This invention relates to gastrin and cholecystokinin (CCK) receptor ligands. (The receptor previously known as the $CCK_B$/gastrin receptor is now termed the $CCK_2$ receptor). The invention also relates to methods for preparing such ligands and to compounds which are useful intermediates in such methods. The invention further relates to pharmaceutical compositions comprising such ligands and methods for preparing such pharmaceutical compositions.

Gastrin and the cholecystokinins are structurally related neuropeptides which exist in gastrointestinal tissue and the central nervous system (Mutt V., *Gastrointestinal Hormones*, Glass G. B. J., ed., Raven Press, New York, p. 169; Nisson G., ibid., p. 127).

Gastrin is one of the three primary stimulants of gastric acid secretion. Several forms of gastrin are found including 34-, 17- and 14-amino acid species with the minimum active fragment being the C-terminal tetrapeptide (TrpMetAspPhe-$NH_2$) which is reported in the literature to have full pharmacological activity (Tracey H. J. and Gregory R. A., *Nature* (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal mobility, gall bladder contraction, pancreatic enzyme secretion and are known to have a trophic action on the pancreas. They also inhibit gastric emptying and have various effects in the central nervous system.

Compounds which bind to cholecystokinin and/or gastrin receptors are important because of their potential pharmaceutical use as antagonists or partial agonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lower gastrin activity or lower acid secretion is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa and the treatment of pancreatic inflammation, biliary tract disease and various psychiatric disorders. Other possible uses are in the potentiation of opiate (for example morphine) analgesia and in the treatment of cancers, especially of the pancreas. Moreover, ligands for cholecystokinin receptors in the brain (so-called $CCK_2$ receptors) have been claimed to possess anxiolytic activity.

PCT/GB99/03733 describes a class of compounds having gastrin antagonist activity. This class of compounds is typically characterised by a 5-membered ring, preferably an imidazole or pyrrole, having two hydrocarbyl substituents and an amide or urea-type substituent.

According to the present invention, there are provided compounds of formula (I)

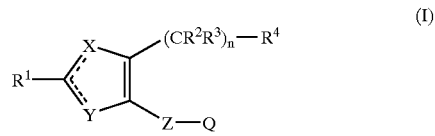

wherein

X and Y are independently =N—, —N($R^5$)— ($R^5$ being selected from H, Me, Et, Pr, Bn, —OH and —$CH_2COOR^6$, wherein $R^6$ represents H, Me, Et, Pr or Bn), =CH—, —S—, or —O—;

$R^1$ is H or $C_1$–$C_{15}$ hydrocarbyl wherein up to three C atoms may optionally be replaced by N, O and/or S atoms, and up to three H atoms may optionally be replaced by halogen atoms;

$R^2$ is selected from H, Me, Et, Pr and OH, each $R^2$ being independently selected from H, Me, Et, Pr and OH when n is greater than 1;

$R^3$ (when n is 1) is selected from H, Me, Et and Pr; or (when n is greater than 1) each $R^3$ is independently selected from H, Me, Et and Pr, or two $R^3$ groups on neighbouring carbon atoms are linked to form a $C_3$ to $C_6$ carbocylic ring, or two $R^3$ groups are absent from neighbouring carbon atoms which are linked by a double bond; or $R^2$ and $R^3$ on the same carbon atom together represent an =O group;

$R^4$ is H or $C_1$–$C_{15}$ hydrocarbyl wherein up to three C atoms may optionally be replaced by N, O and/or S atoms, and up to three H atoms may optionally be replaced by halogen atoms;

Z is a diradical derived from an optionally substituted aromatic or non-aromatic $C_5$ or $C_6$ carbocycle, wherein 1, 2 or 3 C atoms are optionally replaced by N, O and/or S;

Q is a 6-membered aromatic carbocycle (optionally substituted with 1 or 2 V groups and/or 1, 2 or 3 T groups), wherein 1, 2 or 3 C atoms are optionally replaced by N;

V is —CO—NH—$SO_2$—Ph, —$SO_2$—NH—CO—Ph, —$CH_2OH$, or a group of the formula —$R^7U$, (wherein U is —COOH, tetrazolyl, —CONHOH or —$SO_3H$; and $R^7$ is a bond; $C_1$ to $C_6$ hydrocarbylene, optionally substituted by hydroxy, amino or acetamido; —O—($C_1$ to $C_3$ alkylene)-; —$SO_2NR^8$—$CHR^9$—; —CO—$NR^8$—$CHR^9$—, $R^8$ and $R^9$ being independently selected from H and methyl; or —NH—(CO)$_c$—$CH_2$—, c being 0 or 1);

T is $C_1$ to $C_6$ hydrocarbyl, —$NR^{10}R^{11}$ (wherein $R^{10}$ and $R^{11}$ are independently selected from H, Me, Et, Pr or Bn), —OMe, —OH, —$CH_2OH$, halogen or trihalomethyl;

Preferably X and Y are independently =N—, —NH— or —N(OH)—.

Preferably $R^1$ is $C_3$ to $C_{10}$ alicyclic; phenyl, pyridyl, phenyl $C_1$–$C_3$ alkyl or pyridyl $C_1$–$C_3$ alkyl (all optionally substituted with OMe, $NMe_2$, $CF_3$, Me, F, Cl, Br or I); or $C_1$ to $C_8$ alkyl. Alicyclic groups include $C_5$ to $C_8$ cycloalkyl, $C_7$ to $C_{10}$ polycycloalkyl, $C_5$ to $C_8$ cycloalkenyl and $C_7$ to $C_{10}$ polycycloalkenyl, all optionally substituted with methyl. Phenyl $C_1$–$C_3$ alkyl includes, for example, benzyl.

In one aspect of the present invention $R^1$ is cyclohexyl, bicyclooctyl, or tolyl. Most preferably $R^1$ is cyclohexyl, bicyclo[2.2.2]oct-1-yl or tol-2-yl.

Preferably $R^2$ is H, $R^3$ is H and n is 1, 2 or 3.

In certain compounds according to this invention $R^4$ is $C_3$ to $C_{15}$ carbocyclic, optionally substituted with 1, 2 or 3 halogen atoms. In other compounds according to this invention, $R^4$ is —NH—$R^{12}$ or —O$R^{12}$, wherein $R^{12}$ is $C_3$ to $C_{12}$ carbocyclic, optionally substituted with 1, 2 or 3 halogen atoms. Preferably $R^4$ is —O-adamantyl, —O-cycloheptyl, —O-cyclohexyl or —O-phenyl. Most preferably $R^4$ is —O-adamantyl.

In one aspect of the present invention Z is a diradical derived from any one of cyclohexene, benzene, pyridine, pyrazine, pyrimidine, pyridazine, triazine, oxazine, cyclohexane, piperidine, piperazine, morpholine, thiomorpholine, thioxane, dioxane, pyran, dihydropyran, tetrahydropyran, thiopyran, tetrahydrothiopyran, pyrrole, imidazole, pyrazole, thiophene, furan, oxazole, isoxazole, triazole, oxadiazole, thiazole, isothiazole, furazan, thiadiazole, thiophene, pyrrolidine, pyrroline, imidazoline, pyrazolidine, pyrazoline, tetrahydrofuran, tetrahydrothiophene, oxathiolane and oxazolidine.

The diradical may be derived from any two positions on these 5- and 6-membered rings. When Z is a diradical derived from a 6-membered ring, the radical positions may be 1,2-, 1,3-, 1,4-, 1,5-, 1,6-, 2,3-, 2,4-, 2,5-, 2,6-, 3,4-, 3,5-, 3,6-, 4,5-, 4,6- or 5,6-. When Z is a diradical derived from a 5-membered ring, the radical positions may be 1,2-, 1,3-, 1,4-, 1,5-, 2,3-, 2,4-, 2,5-, 3,4-, 3,5- or 4,5-. Preferably, Z is selected from

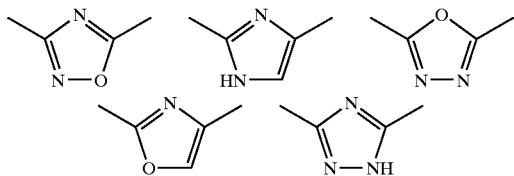

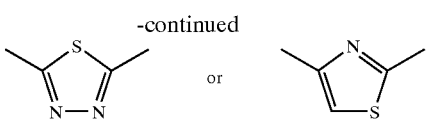

Preferably Q is a phenyl or pyridinyl radical, optionally substituted with —CH$_2$CO$_2$H, —CO$_2$H or tetrazolyl. Accordingly, in one aspect of the present invention there are provided compounds wherein Q is 2-carboxyphenyl, 3-carboxyphenyl, 4-carboxyphenyl, 3-carboxypyridin-2-yl, 4-carboxypyridin-2-yl, 5-carboxypyridin-2-yl, 6-carboxypyridin-2-yl, 2-carboxypyridin-3-yl, 4-carboxypyridin-3-yl, 5-carboxypyridin-3-yl, 6-carboxypyridin-3-yl, 2-carboxypyridin-4-yl, 3-carboxypyridin-4-yl, 2-carboxypyridin-5-yl, 3-carboxypyridin-5-yl, 4-carboxypyridin-5-yl, 6-carboxypyridin-5-yl, 2-carboxypyridin-6-yl, 3-carboxypyridin-6-yl, 4-carboxypyridin-6-yl, 5-carboxypyridin-6-yl or 3-carboxymethylphenyl.

More preferably Q is 3-carboxyphenyl or 3-carboxypyridin-5-yl.

Certain compounds of the present invention exist in various regioisomeric, enantiomeric, tautomeric and diastereomeric forms. It will be understood that the invention comprehends the different regioisomers, enantiomers, tautomers and diastereomers in isolation from each other as well as mixtures.

Compounds of the present invention wherein
(i) X is —NH—
(ii) Y is =N— and
(iii) Z is the 2,5-diradical derived from [1,3,4]oxadiazole (furazan) or [1,3,4] thiadiazole may be conveniently prepared by the route exemplified in Reaction Scheme 1.

Reaction Scheme 1

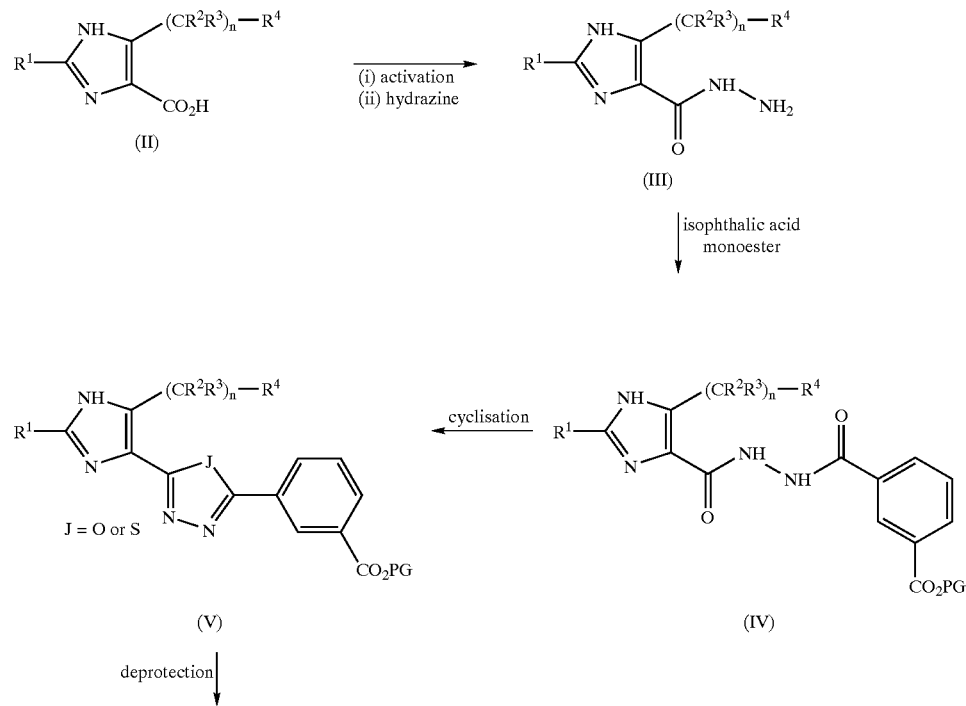

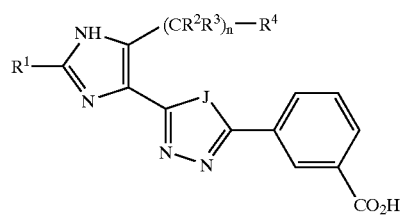

(VI)

A 5-carboxyimidazole derivative (II) is activated with for example EDC and coupled with hydrazine to yield hydrazide (III). The hyrazide (III) is then coupled with for example EDC-activated isophthalic acid monoester. The reaction product (IV) is cyclised using either Lawesson's reagent, to furnish compounds wherein Z is a [1,3,4] thiadiazole, or Ph₃P/CCl₄/DBU to furnish compounds wherein Z is a furazan. Deprotection affords the target carboxylic acid (VI).

Compounds of the present invention wherein (i) X is —NH—
(ii) Y is =N— and
(iii) Z is the 3,5-diradical derived from triazole may be conveniently prepared by the route exemplified in Reaction Scheme 2.

Reaction Scheme 2

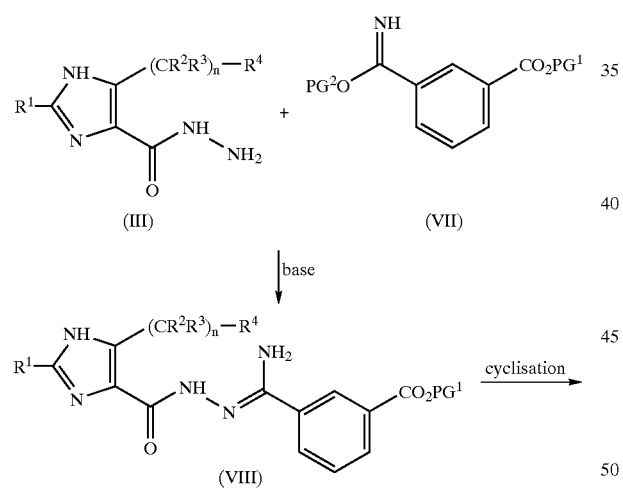

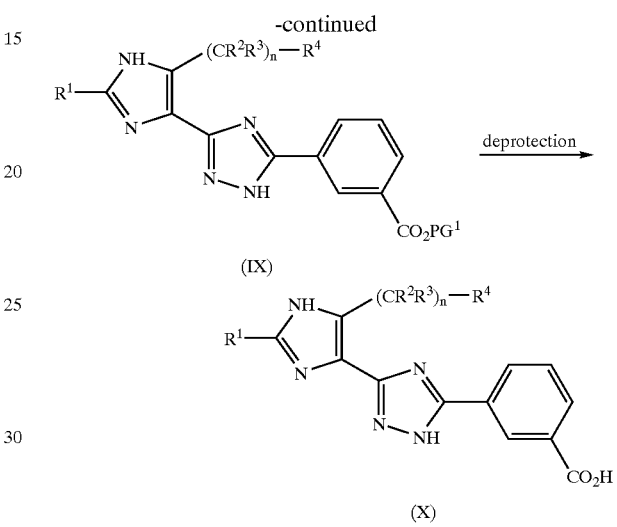

The hydrazide (III), prepared as shown in Reaction Scheme 1, is coupled with amidate (VII) to yield an amidine derivative (VIII). Cyclisation of the amidine derivative (VIII) affords triazole ester (IX). Finally, the target carboxylic acid (X) is unmasked using a convenient method. For example, when the carboxylic acid is masked as a benzyl ester, catalytic hydrogenation finishes the requisite carboxylic acid (X).

Compounds of the present invention wherein (i) X is —NH—
(ii) Y is =N— and
(iii) Z is the 2,5-diradical derived from oxazolidine may be conveniently prepared by the route exemplified in Reaction Scheme 3.

Reaction Scheme 3

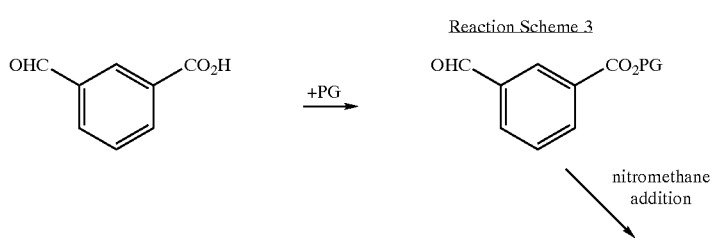

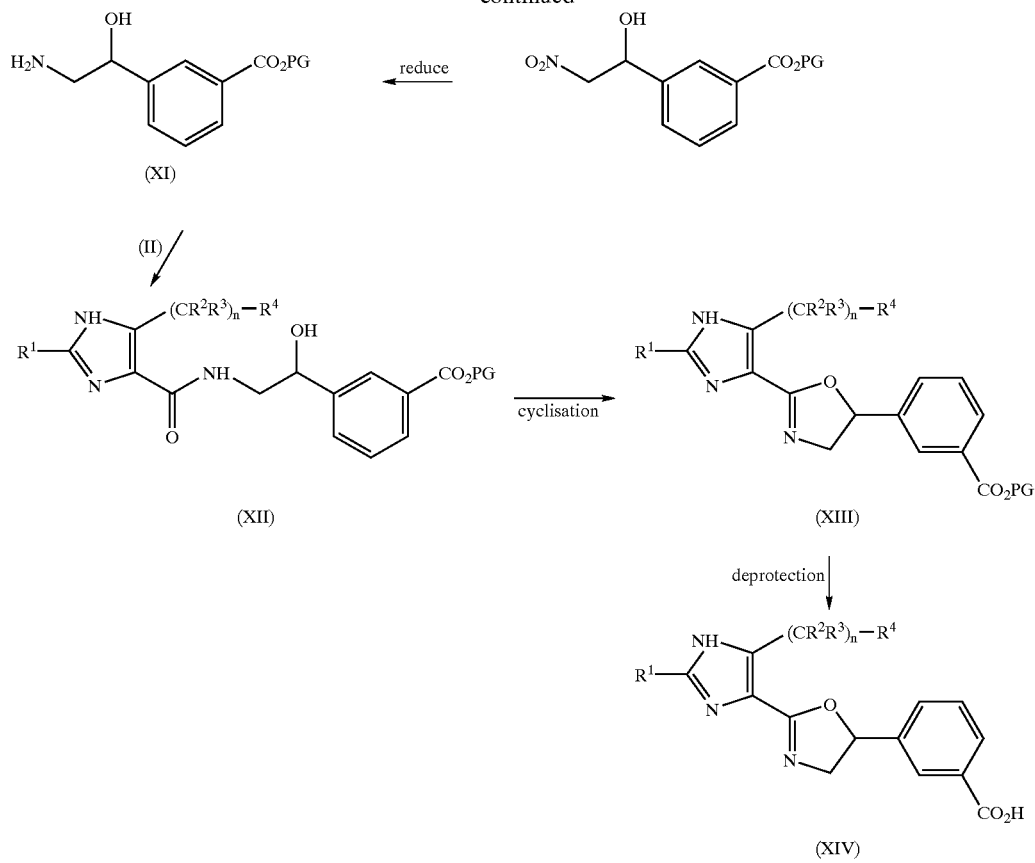

Amine (XI) is prepared from the commercially available 3-carboxybenzaldehyde (Aldrich Chemical Co.) by for example the route shown in Reaction Scheme 3. The amine (XI) is then coupled with 3-carboxyimidazole derivative (II) to yield amide (XII). Cyclisation of (XII) affords oxazolidine ester (XIII), which is then deprotected to afford the target carboxylic acid (XIV). For example, when the carboxylic acid is masked as a methyl ester in compound (XIII), saponification using LiOH in methanol affords the requisite acid (XIV).

Compounds of the present invention wherein (i) X is =N—

(ii) Y is —N(OH)— and (iii) Z is the 2,5-diradical derived from furazan may be conveniently prepared by the route exemplified in Reaction Scheme 4.

Reaction Scheme 4

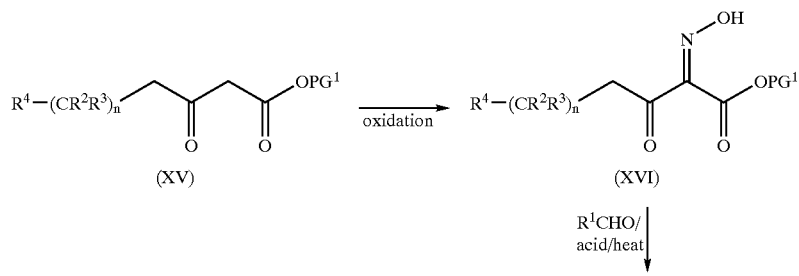

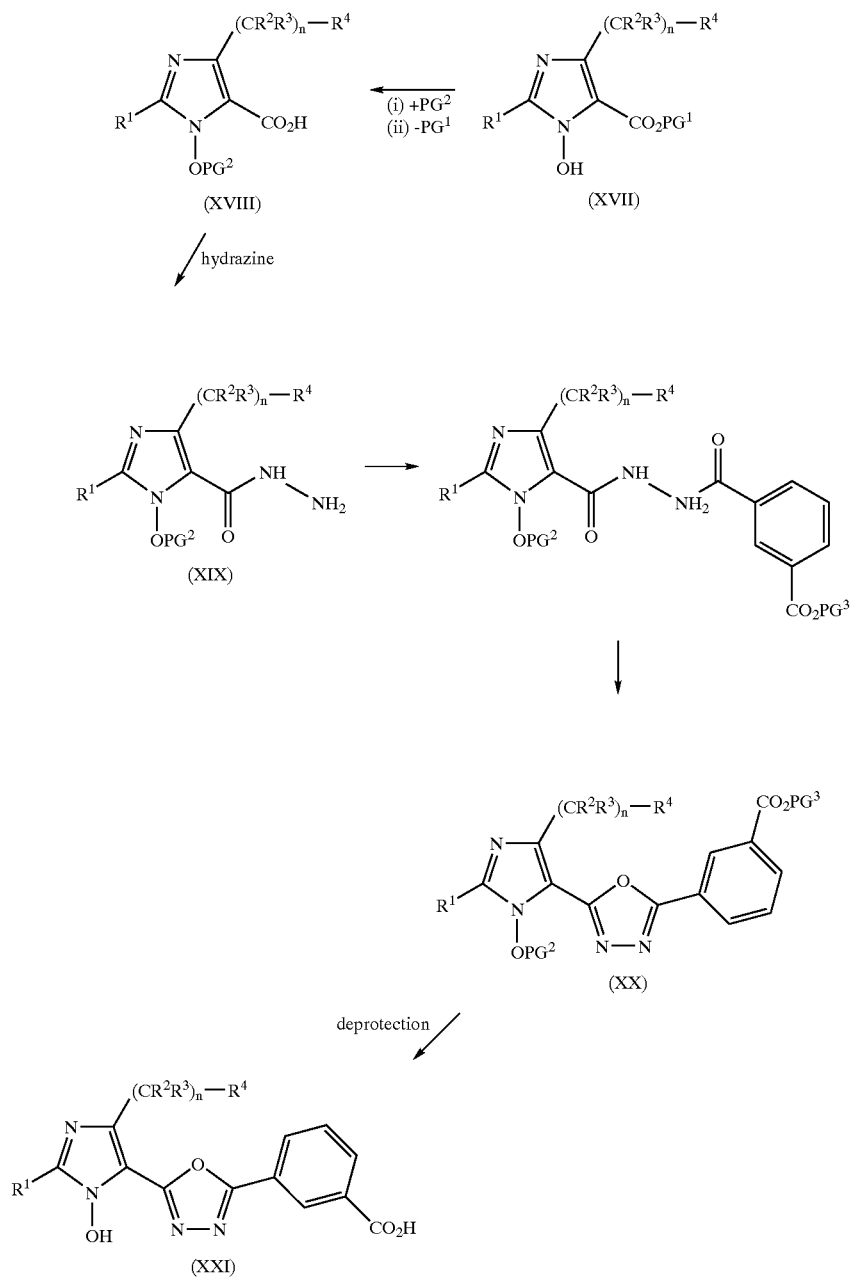

β-Ketoester (XV) is oxidised with, for example, sodium nitrite. The resulting α-hydroxyimino-β-ketoester (XVI) is reacted with a suitable R¹—CHO compound and concomitantly cyclised to hydroxyimidazole (XVII). Following protection of the hydroxyl group on compound (XVII), the ester is chemoselectively converted to the corresponding carboxylic acid (XVIII), which is then coupled with hydrazine to yield a hydrazide (XIX). The hydrazide is then converted to furazan (XX) by the route described and shown in Reaction Scheme 1. Final deprotection yields the requisite N-hydroxyimidazole (XXI). It will be readily apparent to the skilled person that hydrazide (XIX) may also be converted to a compound wherein Z is the 2,5-diradical derived from [1,3,4]dithiazole by the alternative route described in Reaction Scheme 1.

Compounds of the present invention wherein (i) X is —NH—

(ii) Y is =N— and (iii) Z is the 2,4-diradical derived from oxazole may be conveniently prepared by the route exemplified in Reaction Scheme 5.

Reaction Scheme 5

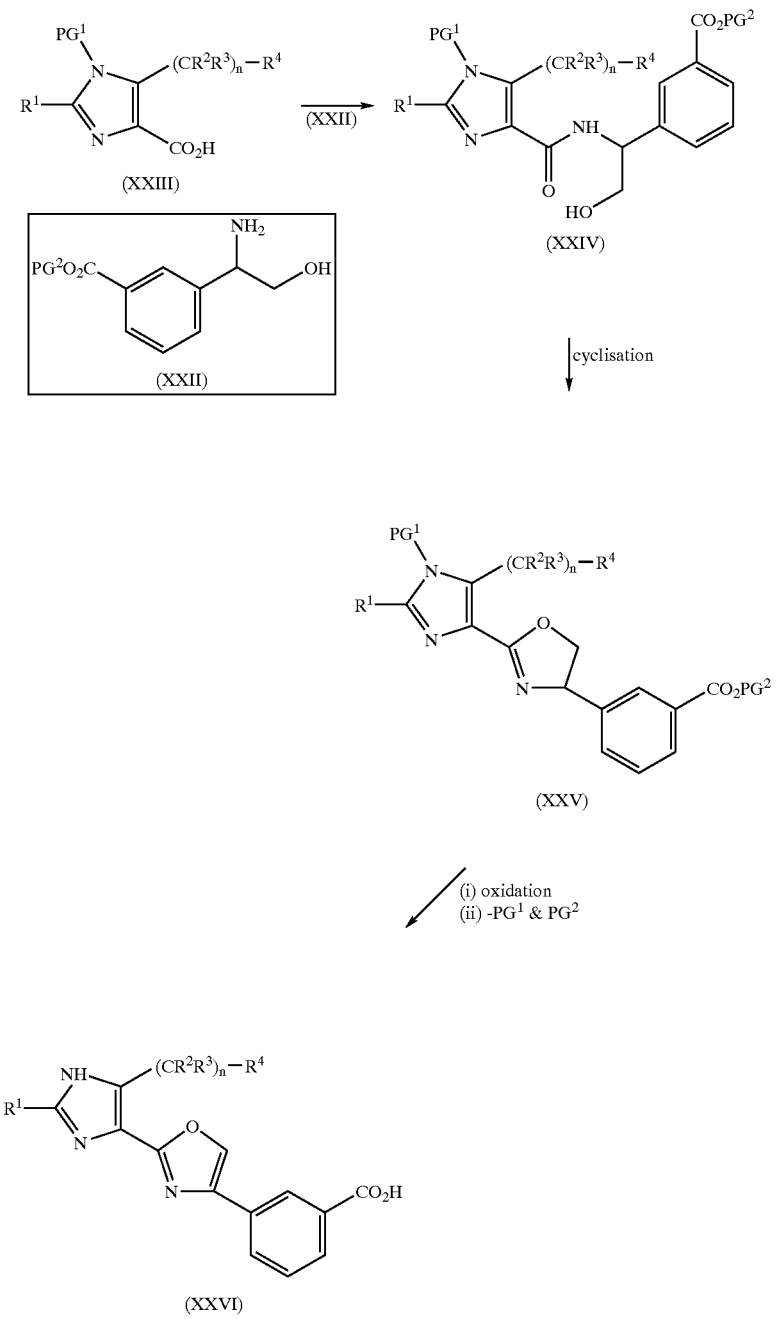

Hydroxyamine (XXII) is coupled with a suitably N-protected (e.g. Boc-protected) 4-carboxyimidazole derivative (XXIII). The resultant amide (XXIV) is cyclised to yield oxazolidine (XXV). Finally, oxidation with for example $NiO_2$, followed by deprotection furnishes the requisite oxazole (XXVI). It will be readily apparent to the skilled person that oxazolidine (XXV) may be converted to a compound of the present invention wherein Z is the 2,4-diradical derived from oxazolidine by simple deprotection of (XXV).

Compounds of the present invention wherein (i) X is —NH—

(ii) Y is =N— and (iii) Z is the 3,5-diradical derived from [1,2,4]oxadiazole may be conveniently prepared by the route exemplified in Reaction Scheme 6.

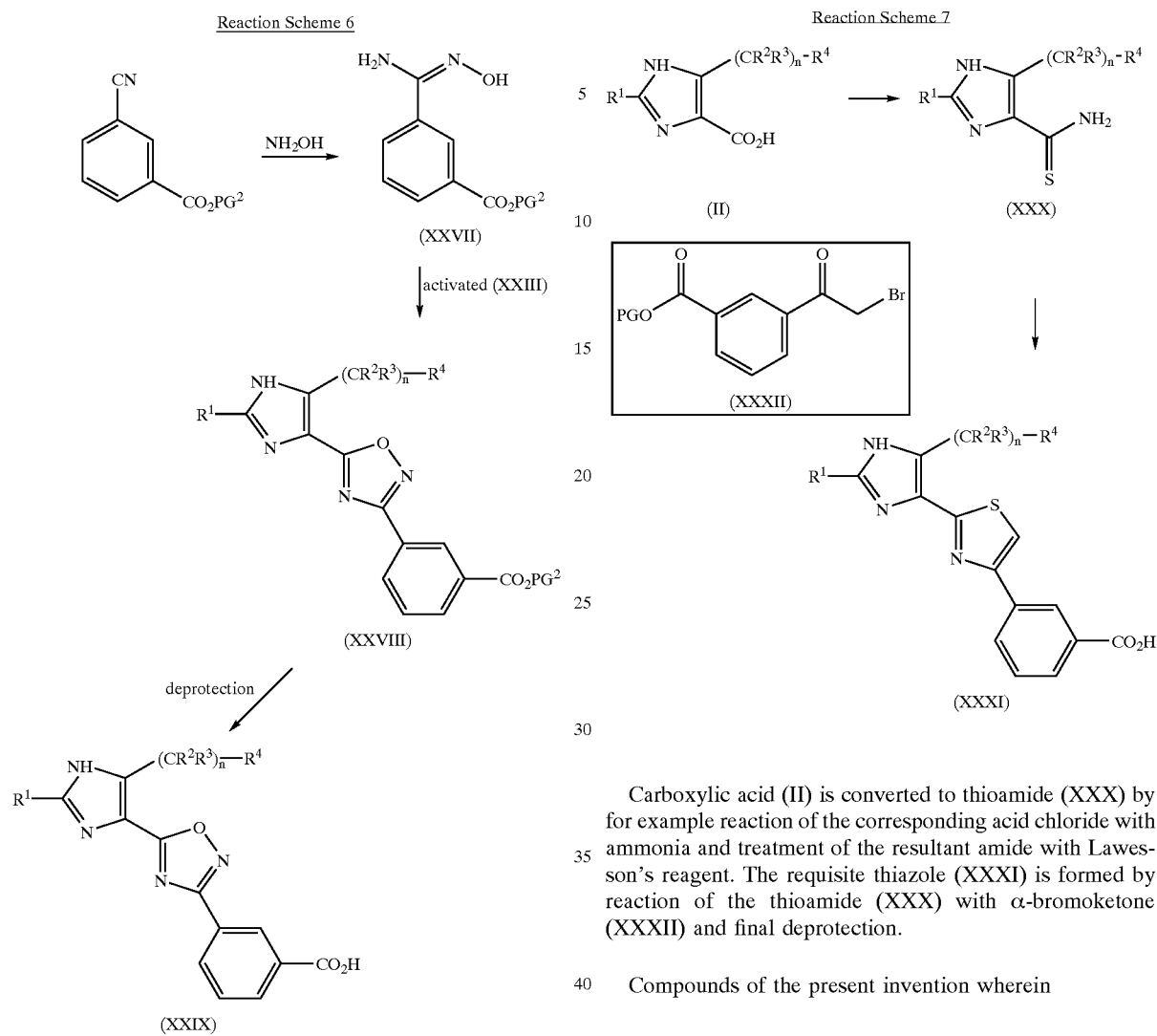

Amidoxime derivative (XXVII) is coupled with the N-protected 3-carboxyimidazole (XXIII) after activation of the carboxylic acid with for example CDI. The resultant coupled product is cyclised in situ to [1,2,4]oxadiazole (XXVIII) after further activation and heating. The requisite carboxylic acid (XXIX) is unmasked by conversion of the ester group to an acid group by standard methods. For example, in the case of a benzyl ester, hydrogenation yields the carboxylic acid (XXIX).

Compounds of the present invention wherein (i) X is —NH—

(ii) Y is =N— and (iii) Z is the 2,4-diradical derived from thiazole may be conveniently prepared by the route exemplified in Reaction Scheme 7.

Carboxylic acid (II) is converted to thioamide (XXX) by for example reaction of the corresponding acid chloride with ammonia and treatment of the resultant amide with Lawesson's reagent. The requisite thiazole (XXXI) is formed by reaction of the thioamide (XXX) with α-bromoketone (XXXII) and final deprotection.

Compounds of the present invention wherein (i) X is —NH—

(ii) Y is =N— and (iii) Z is the 2,4-diradical derived from imidazole may be conveniently prepared by the route exemplified in Reaction Scheme 8.

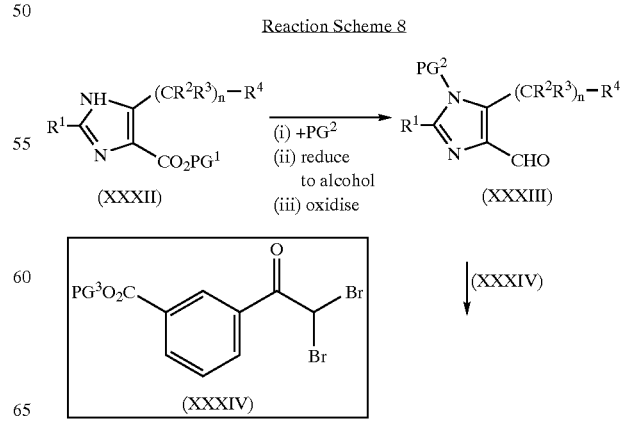

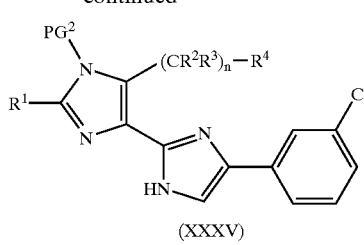

(XXXV)

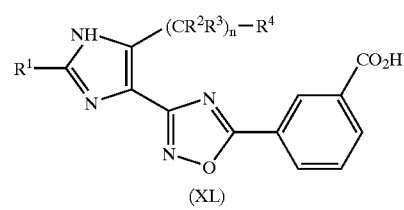

(XXXVI)

Ester (XXXII) was converted aldehyde (XXXIII) by for example protection of the 1-position on the imidazole ring (e.g. with a benzyl group), reduction of the ester to an alcohol, and oxidation to the aldehyde (XXXIII). Reaction of aldehyde (XXXIII) with α-dibromoketone (XXXVI) provides biimidazole (XXXV), which affords the requisite biimidazole acid (XXXVI) after final deprotection.

Compounds of the present invention wherein (i) X is —NH—

(ii) Y is =N— and (iii) Z is the 3,5-diradical derived from [1,2,4]oxadiazole may be conveniently prepared by the route exemplified in Reaction Scheme 9.

Reaction Scheme 9

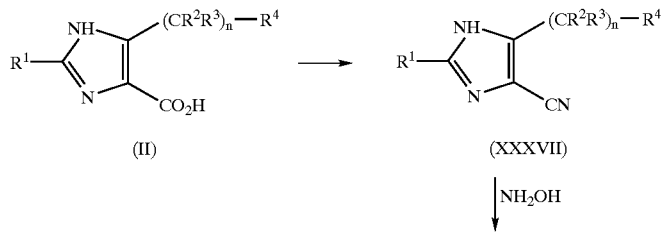

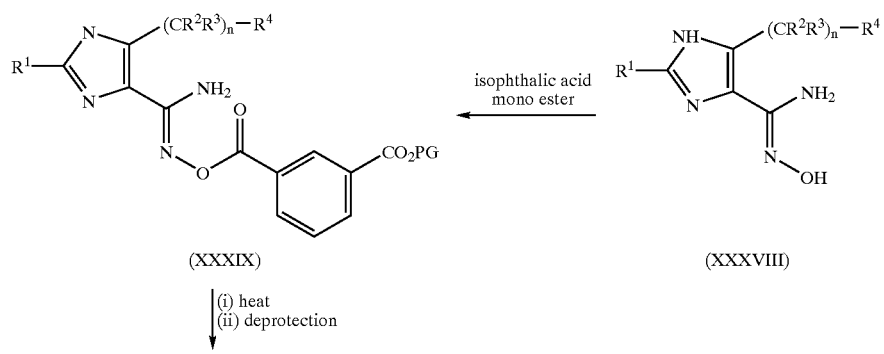

(XL)

Carboxylic acid (II) is converted to the corresponding nitrile (XXXVII) by for example conversion to an amide via the acid chloride, and then reaction of the amide with for example $SOCl_2$. Reaction of nitrile (XXXVII) with hydroxylamine produces hydroxylamidine (XXXVIII) which furnishes oxadiazole precursor (XXXIX) after coupling with for example CDI-activated isophthalic acid monoester. Cyclisation of (XXXIX) and final deprotection yields the requisite oxadiazole (XL).

Hence, the present invention provides methods of making compounds according to formula (I).

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, 1985, pp. 112–176, and *Drugs*, 1985, 29, pp. 455–473.

Pro-drug forms of the pharmacologically-active compounds of the invention will generally be compounds according to formula (I) having an acid group which is esterified or amidated. Included in such esterified acid groups are groups of the form —$COOR^a$, wherein $R^a$ is $C_1$ to $C_5$ alkyl, phenyl, substituted phenyl, benzyl, substituted benzyl, or one of the following:

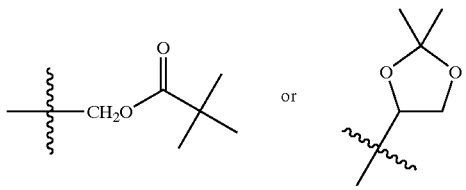

Amidated acid groups include groups of the formula —$CONR^bR^c$, wherein $R^b$ is H, $C_1$ to $C_5$ alkyl, phenyl, substituted phenyl, benzyl, or substituted benzyl, and $R^c$ is —OH or one of the groups just recited for $R^b$.

Compounds of formula (I) having an amino group may be derivatised with a ketone or an aldehyde such as formaldehyde to form a Mannich base. This will hydrolyse with first order kinetics in aqueous solution.

Another aspect of the present invention is a pharmaceutical composition comprising a compound of formula (I) substantially as described herein before with a pharmaceutically acceptable diluent or carrier.

Yet another aspect of the present invention is a method of making a pharmaceutical composition comprising a compound of formula (I) substantially as described herein before, comprising mixing said compound with a pharmaceutically acceptable diluent or carrier.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 μg/kg and 50 mg/kg, especially between 10 μg/kg and 10 mg/kg, eg. between 100 μg/kg and 2 mg/kg.

In a further aspect of the present invention there are provided pharmaceutical compositions comprising a compound according to formula (I) and a proton pump inhibitor. Compositions comprising a CCK/gastrin antagonist and a proton pump inhibitor are described in International patent application WO93/12817, incorporated herein by reference.

In one aspect of the present invention the proton pump inhibitor is omeprazole which is 5-methoxy-2-[[(4-methoxy-3,5-dimethyl-2-pyridinyl)-methyl]sulfinyl]-1H-benzimidazole;

BY308;

SK & 95601 which is 2-[[(3-chloro-4-morpholino-2-pyridyl)methyl]sulfinyl]-5-methoxy-(1H)-benzimidazole;

SK & 96067 which is 3-butyryl-4-(2-methylphenylamino)-8-methoxyquinoline;

5-trifluoromethyl-2-[4-methoxy-3-methyl-2-pyridyl-methyl]-thio-[1H]-benzimidazole;

or pharmaceutically acceptable salts thereof.

These proton pump inhibitors are described and claimed in U.S. Pat. Nos. 4,472,409 and 4,255,431. These patents are incorporated herein by reference.

In a further aspect of the present invention, the proton pump inhibitor is lansoprazole which is 2-[[[3-methyl-4-(2,2,2-trifluoroethoxy)-2-pyridinyl]methyl]sulfinyl]-1H-benzimidazole;

pantoprazole which is 5-(difluoromethoxy)-2-[[(3,4-dimethoxy-2-pyridinyl)methyl]sulfinyl]-1H-benzimidazole;

perprazole;

rabeprazole which is 2-[[4-(3-methoxypropoxy)-3-methylpyridin-2-yl]methylsulfinyl]-1H-benzimidazole;

[[4-(2,2,2-trifluoroethoxy)-3-methyl-2-pyridyl]-methyl] sulfenamide;

(Z)-5-methyl-2-[2-(1-naphthyl)ethenyl]-4-piperidindpyridine HCl;

2-(4-cyclohexyloxy-5-methylpyridin-2-yl)-3-(1-naphthyl)-1-propanol;

methyl 2-cyano-3-(ethylthio)-3-(methylthio)-2-propenoate;

2-((4-methoxy-2-pyridyl)methylsulphinyl)-5-(1,1,2,2-tetrafluoroethoxy)-1H-benzimidazole sodium;

2-[[[4-(2,2,3,3,4,4,4-heptafluorobutoxy)-2-pyridyl] methyl)sulfinyl]-1H-thieno [3,4-d]imidazole;

2-[[[4-(2,2,2-trifluoroethoxy)-3-methyl-2-pyridyl] methyl]sulfinyl]-1H-benzimidazole;

2-[[[4-(2,2,2-trifluoroethoxy)-3-methyl-2-pyridyl] methyl]sulfinyl]-1H-benzimidazole;

2-methyl-8-(phenylmethoxy)-imidazo(1,2-A)-pyridine-3-acetonitrile;

(2-((2-dimethylaminobenzyl)sulfinyl)-benzimidazole);

4-(N-allyl-N-methylamino)-1-ethyl-8-((5-fluoro-6-methoxy-2-benzimidazolyl) sulfinylmethyl)-1-ethyl 1,2,3,4-tetrahydroquinolone;

2-[[(2-dimethylaminophenyl)methyl]sulfinyl]-4,7-dimethoxy-1H-benzimidazole;

2-[(2-(2-pyridyl)phenyl)sulfinyl)-1H-benzimidazole;

(2-[(2-amino-4-methylbenzyl)sulfinyl]-5-methoxybenzo [d]imidazole;

(4(2-methylpyrrol-3-yl)-2-guanidisothiazole);

4-(4-(3-(imidazole)propoxy)phenyl)-2-phenylthiazole;

(E)-2-(2-(4-(3-(dipropylamino)butoxy)phenyl)-ethenyl) benzoxazole;

(E)-2-(2-(4-(3-(dipropylamino)propoxy)phenyl)ethenyl)-benzothiazole;

Benzeneamine, 2-[[(5-methoxy-1H-benzimidazol-2-yl) sulfinyl]methyl]-4-methyl-;

Pumilacidin A;

2,3-dihydro-2-methoxycarbonylamino-1,2-benzisothiazol-3-one;

2-(2-ethylaminophenylmethylsulfinyl)-5,6-dimethoxybenzimidazole;

2-methyl-8-(phenylmethoxy)imidazo[1,2-a)pyridine-3-acetonitrile;

3-amino-2-methyl-8-phenylmethoxyimidazo[1,2-a)-pyrazine HCl;

2-[[(3-chloro-4-morpholino-2-pyridyl)methyl]-sulfinyl)-5-methoxy-(1H)-benzimidazole;

[3-butyryl-4-(2-methylphenylamino)-8-methoxy-quinoline);

2-indanyl 2-(2-pyridyl)-2-thiocarbamoylacetate HCl;

2,3-dihydro-2-(2-pyridinyl)-thiazolo (3,2-a)-benzimidazole;

3-cyanomethyl-2-methyl-8-(3-methyl-2-butenyloxy)-(1, 2-a)imidazopyridine;

zinc L-carnosine;

or pharmaceutically acceptable salts thereof.

Rabeprazole is described in U.S. Pat. No. 5,045,552. Lansoprazole is described in U.S. Pat. No. 4,628,098. Pantoprazole is described in U.S. Pat. No. 4,758,579. These patents are incorporated herein by reference.

Preferably, the proton pump inhibitor is selected from (RS)-rabeprazole, (RS)-omeprazole, lansoprazole, pantoprazole, (R)-omeprazole, (S)-omeprazole, perprazole, (R)-rabeprazole, (S)-rabeprazole, or the alkaline salts thereof. The alkaline salts may be, for example, the lithium, sodium, potassium, calcium or magnesium salts.

Compositions of this invention comprising a compound of formula (I) and a proton pump inhibitor may be administered as described above. Preferably the dose of each of the active ingredients in these compositions will be equal to or less than that which is approved or indicated in monotherapy with said active ingredient.

In another aspect of this invention, there is provided a kit comprising a compound of formula (I) and a proton pump inhibitor. The kit is useful as a combined preparation for simultaneous, separate or sequential use in the treatment of patients suffering from gastrointestinal disorders.

In yet a further aspect of the present invention there is provided a method of making a pharmaceutical composition comprising a compound of formula (I) substantially as described herein before and a proton pump inhibitor, comprising mixing said compound and said proton pump inhibitor with a pharmaceutically acceptable carrier or diluent.

The term "hydrocarbyl" is used herein to refer to monovalent groups consisting of carbon and hydrogen. Hydrocarbyl groups thus include alkyl, alkenyl and alkynyl groups (in both straight and branched chain forms), cycloalkyl (including polycycloalkyl), cycloalkenyl and aryl groups, and combinations of the foregoing, such as alkylcycloalkyl, alkylpolycycloalkyl, alkylaryl, alkenylaryl, alkynylaryl, cycloalkylaryl and cycloalkenylaryl groups.

Where reference is made to a carbon atom of a hydrocarbyl group being replaced by a N, O or S atom, what is intended is that

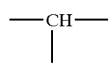

is replaced by

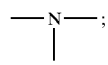

or that —$CH_2$— is replaced by —O— or —S—.

A "carbocyclic" group, as the term is used herein, comprises one or more closed chains or rings, which consist entirely of carbon atoms. Carbocyclic groups thus include aryl groups (such as phenyl, naphthyl, indanyl, fluorenyl, (1,2,3,4)-tetrahydronaphthyl, indenyl and isoindenyl, and substituted derivatives thereof), and also alicyclic groups. The term "alicyclic group" refers to a carbocyclic group which does not contain an aromatic ring, and thus includes groups such as cyclopropyl, cyclobutyl, cyclopentyl, cyclohexyl, cyclohexenyl, adamantyl, norbornyl, bicyclo[2.2.2]octyl, norbornenyl and bicyclo[2.2.2]octenyl, and also groups (such as adamantanemethyl and methylcyclohexyl) which contain both alkyl or alkenyl groups in addition to cycloalkyl or cycloalkenyl moieties.

The term "aryl" is used herein to refer to an aromatic group, such as phenyl or naphthyl, or a heteroaromatic group, such as pyridyl, pyrrolyl, or furanyl.

The term "alkyl" is used herein to refer to both straight and branched chain forms.

When reference is made herein to a substituted carbocyclic group (such as substituted phenyl) or a substituted heterocyclic group, the substituents are preferably from 1 to 3 in number and selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, aryl, aryl($C_1$ to $C_6$)alkyl, ($C_1$ to $C_6$ allyl)aryl, halo, $C_1$ to $C_6$ alkylhalo, sulphamoyl, tetrazolyl and cyano.

Most usually, substituents will be selected from $C_1$ to $C_6$ alkyl, $C_1$ to $C_6$ alkoxy, thio, $C_1$ to $C_6$ alkylthio, carboxy, carboxy($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy ($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, halo, $C_1$ to $C_6$ alkylhalo, sulphamoyl, tetrazolyl and cyano.

The term "halogen" is used herein to refer to any of fluorine, chlorine, bromine and iodine. Most usually, however, halogen substituents in the compounds of the invention are chlorine and fluorine substituents.

The term "suitably protected" used herein refers to the use of any suitable protecting group to protect a functional group. Such protecting groups are denoted as PG, $PG^1$, $PG^2$, $PG^3$ etc. in the Reaction Schemes illustrated above. Suitable protecting groups will be readily apparent to the skilled person and may be found in, for example, Kocienski, *Protecting Groups*, Thieme, New York, 1994. For example, in the case of hydroxyl groups, suitable protecting groups may include esters, ethers (e.g. silyl ethers or alkyl ethers) or acetals. Some specific examples of typical hydroxyl protecting groups are allyl, Aloc, benzyl, BOM, t-butyl, trityl, TBS, TBDPS, TES, TMS, TIPS, PMB, MEM, MOM, MTM, and THP. In the case of nitrogen atoms, suitable protecting groups may include Boc, Aloc, Troc, benzyl, allyl, Fmoc or silyl. In the case of carboxylic acids, suitable protecting groups may include esters (e.g. benzyl, allyl, methyl or ethyl esters).

The term "activated" used herein in connection with carboxylic acids refers to any activated derivative of a carboxylic acid. Methods of activating carboxylic acids will be known to the skilled artisan and may include activation using EDC, CDI or DCC (optionally in the presence of nucleophilic catalysts such as DMAP), conversion to an acid halide such as an acid chloride (e.g. using $SOCl_2$ or oxalyl chloride) or conversion to an activated ester (such as a phenyl or pentafluorophenyl ester).

The invention is now further illustrated by means of the following Examples. All reactions were performed under an atmosphere of dry argon unless otherwise stated. Dichloromethane (DCM) was freshly distilled from calcium hydride. Anhydrous tetrahydrofuran (THF) and N,N-dimethylformamide (DMF) were used.

EXAMPLE 1

Reaction Scheme 5

3-{2-[5-(Adamantan-1-yloxymethyl)-2-cyclohexyl-1H-imidazol-4-yl}-oxazol-4-yl}-benzoic acid Step a. (Adamantan-1-yloxy)-acetic acid. A mixture of (adamantan-1-yloxy)-acetic acid ethyl ester (A. F. Noels et al. Tetrahedron, 1982, 38, 2733) (7.29 g, 29 mmol) and potassium hydroxide (2.60 g, 46 mmol) in water-ethanol (1:2 mixture, 180 ml) was heated at reflux for 2 h. The mixture was cooled, then concentrated in vacuum and acidified with concentrated hydrochloric acid. The resultant white precipitate was dissolved in ethyl acetate (200 ml). The solution was washed with brine (2×200 ml), dried ($MgSO_4$) and the solvent was evaporated to afford white crystalline solid (5.85 g 92%). $^1$H NMR (300 MHz, $CDCl_3$) 4.08 (2H, s), 2.20–1.58 (15H, m).

Step b. 4-(Adamantan-1-yloxy)-3-oxo-2-(triphenyl-$l^5$-phosphanylidene)-butyric acid benzyl ester. Oxalyl chloride (18.6 ml, 0.214 mol) was added to a solution of the product of step a (39.13 g, 0.178 mol) in DCM (800 ml) containing catalytic amount of DMF at room temperature. The mixture was stirred at room temperature for 1 h, then the solvent was evaporated. The residue was dissolved in benzene (100 ml) and added dropwise to a solution of benzyl (triphenylphosphoranylidene)acetate (72.9 g, 0.178 mol) and N,O-bis(trimethylsilyl)acetamide (53.2 ml, 0.215 mol) in benzene (300 ml) at 0° C. The mixture was allowed to warm to room temperature, and stirred for 16 h. The reaction mixture was diluted with ethyl acetate (500 ml), washed with 5% aqueous potassium hydrogen sulfate (500 ml), 10% sodium carbonate (500 ml), brine (300 ml), dried ($MgSO_4$) and the solvent was evaporated. The residue was triturated with diethyl ether to afford white solid (93.83 g, 98%). $^1$H NMR (300 MHz, CDCl$_3$) 7.64–6.94 (20H, m), 4.74 (2H, s), 4.72 (2H, s), 2.08–1.57 (15H, m).

Step c. 4-(Adamantan-1-yloxy)-2,3-dioxo-butyric acid benzyl ester monohydrate. To a vigorously stirred solution of the product of step b (12.0 g, 20.0 mmol) in DCM/water (1:1 mixture, 320 ml) were added tetrabutylammonium bromide (645 mg, 2.00 mmol) and potassium peroxymonosulfate (OXONE) (24.7 g, 40.0 mmol) at 0° C. The mixture was stirred at room temperature for 48 h, the organic layer was separated, washed with water (3×100 ml), brine (100 ml), dried (MgSO$_4$) and the solvent was evaporated in vacuum. The residue was purified by flash chromatography (silica, hexane/ethyl acetate 1:1) to afford the product as pale yellow oil (6.1 g, 81%). $^1$H NMR (300 MHz, CDCl$_3$) 7.33 (5H, m), 5.26 (2H, s), 4.98 (2H, br s), 4.30 (2H, s), 2.14 (3H, br s), 1.72–1.54 (12H, m).

Step d. 5-(Adamantan-1-yl-oxymethyl)-2-cyclohexyl-1H-imidazole-4-carboxylic acid benzyl ester. To a slurry of the product of step c (1.70 g, 4.54 mmol) and ammonium acetate (3.40 g, 45.4 mmol) in acetic acid (20 ml) was added cyclohexanecarboxaldehyde (1.10 ml 9.08 mmol). The mixture was stirred in an oil bath heated at 70° C. for 2 h. The solution was cooled to room temperature and the acetic acid was evaporated in vacuum. The residue was dissolved in ethyl acetate (30 ml), saturated sodium bicarbonate (100 ml) was slowly added and the mixture was stirred for 30 min. The organic layer was separated, washed with sodium bicarbonate (30 ml), brine (30 ml), dried (MgSO$_4$) and the solvent was evaporated. The crude product was purified by flash column chromatography (silica, DCM/ethyl acetate 4:1) to afford colourless foam (1.0 g, 49%). $^1$H NMR (CDCl$_3$) 7.40 (5H, m), 5.30 (2H, s), 4.76 (2H, br s), 2.79 (1H, m), 2.14 (3H, br s), 2.05 (2H, m), 1.85–1.26 (20H, m).

Step e. 5-(2-Adamantan-1-yl-oxymethyl)-2-cyclohexyl-imidazole-1,4-dicarboxylic acid 4-benzyl ester1-tert-butyl ester. To a solution of the product of step d above (2.4 g, 5.35 mmol) in anhydrous dioxan (50 ml) were added di-tert-butyl dicarbonate (1.52 g, 6.96 mmol) and 4-dimethylaminopyridine (DMAP) (0.1 g). The solution was stirred at room temperature overnight then evaporated to dryness. The major isomer (2.52 g, 86%) (lower R$_f$) was isolated by flash chromatography (silica, DCM/ethyl acetate 97:3). $^1$H NMR (300 MHz, CDCl3) 7.44 (2H, m), 7.34 (3H, m), 5.37 (2H, s), 4.96 (2H, s), 2.99 (1H, tt), 2.64 (3H, s), 1.85 (2H, m), 1.72 (2H, m), 1.70 (3H, m), 1.60 (9H, s), 1.53 (12H, m).

Step f. 5-(2-Adamantan-1-yl-oxymethyl)-2-cyclohexyl-imidazole-1,4-dicarboxylic acid 1-tert-butyl ester. 10% Palladium on charcoal (250 mg) was added to a solution of the product of the previous step (2.52 g, 4.60 mmol) in THF/methanol (1:1 mixture, 50 ml) and the mixture was stirred under an atmosphere of hydrogen for 3 h. The catalyst was removed by filtration and the filtrate evaporated to afford the product as a white solid (1.99 g, 95%). $^1$H NMR (300 MHz, d$_6$-DMSO) 4.91 (2H, s), 2.95 (1H, tt), 2.06 (3H, s), 1.81 (4H, m), 1.62 (6H, s), 1.59 (9H, s), 1.51 (9H, m), 1.27 (3H, m).

Step g. 3-(1-amino-2-hydroxy-ethyl)-benzoic acid methyl ester. 3-(1-N-tert-butyloxycarbonylamino-2-hydroxyethyl)-benzoic acid methyl ester was prepared according to the procedure of B. P. Roques et al (J. Med. Chem. 1994 37, 1339) and deprotected on stirring in a 4M solution of HCl in dioxan at room temperature for 2 h. Evaporation of the solvent gave the amine hydrochloride salt in quantitative yield. $^1$H NMR (300 MHz, d$_6$-DMSO) 8.50 (3H, br s), 8.10 (1H, s), 7.95 (1H, d), 7.76 (1H, d), 7.58 (1H, t), 5.53 (1H, t), 4.40 (1H, t), 3.87 (3H, s), 3.73 (2H, m).

Step h. 5-(Adamantan-1-yloxymethyl)-2-cyclohexyl-4-(2-hydroxy-1-(3-methoxycarbonyl-phenyl)-ethylcarbamoyl-imidazole-1-carboxylic acid tert-butyl ester. To a solution of the acid from step f above (2.90 g, 6.33 mmol) and the amine hydrochloride from step g (1.52 g, 6.56 mmol) in dry DMF (30 ml) were added 1-hydroxybenzotriazole (HOBt) (1.06 g, 7.87 mmol), 1-(3-dimethylaminopropyl-3-ethylcarbodiimide hydrochloride (EDC) (1.51 g, 7.87 mmol) and diisopropylethylamine (2.28 ml, 13.12 mmol). The solution was stirred at room temperature for 68 h then concentrated in vacuo and the residue partitioned between water and ethyl acetate. The organic layer was washed with water, 1M HCl and brine, dried (Na$_2$SO$_4$) and evaporated. The crude material was purified by flash chromatography (Silica, DCM/ethyl acetate 3:1) to give the product as a white solid (1.42 g, 35%). $^1$H NMR (300 MHz, CDCl$_3$) 8.06 (1H, s), 7.98 (1H, d), 7.90 1H, d), 7.59 (1H, d), 7.46 (1H, t), 5.26 (1H, m), 5.09 (2H, q), 4.00 (2H, m), 3.92 (3H, s), 3.00 (1H, tt), 2.75 (1H, br t), 2.09 (3H, br s), 1.44 (4H, m), 1.72 (6H, m), 1.65 (9H, s), 1.58 (10H, m), 1.33 (4H, m).

Step i. 5-(Adamantan-1-yloxymethyl)-2-cyclohexyl-4-(4-(3-methoxycarbonyl-phenyl)-4,5-dihydro-oxazol-2-yl]-imidazole-1-carboxylic acid tert-butyl ester. To a solution of the product from step d above (646 mg, 1 mmol) in acetonitrile (10 ml) was added triphenyl, phosphine (760 mg, 2.9 mmol) followed by diisopropylethylamine (540 μl, 3.1 mmol) then carbon tetrachloride (270 μl, 2.8 mmol). After stirring for 20 h saturated sodium bicarbonate solution was added and the mixture extracted three times with DCM. The combined extracts were dried (Na$_2$SO$_4$) and evaporated. The crude product was purified by flash chromatography (Silica, DCM/ethyl acetate 4:1). Yield 0.53 g (84%). $^1$H NMR (300 MHz, CDCl3) 7.97 (1H, s), 7.96 (1H, d), 7.53 (1H, d), 7.40 (1H, t), 5.43 (1H, dd), 5.20 (1H, d), 4.96 (1H, d), 4.78 (1H, dd), 4.22 (1H, t), 3.90 (3H, s), 3.05 (1H, tt), 2.03 (3H, s), 1.95 (2H, m), 1.84 (2H, m), 1.67 (17H, s), 1.52 (6H, q), 1.32 (4H, m).

Step j. 5-(Adamantan-1-yloxymethyl)-2-cyclohexyl-4[4-(3-methoxycarbonyl-phenyl)-oxazol-2-yl]-imidazole-1-carboxylic acid tert-butyl ester. To a solution of the product from step d above (342 mg, 0.54 mmol) in DCM (25 ml) was added nickel peroxide (500 mg) and the black suspension was stirred at room temperature overnight. Filtration and evaporation afforded essentially pure oxazole (330 mg, 97%). $^1$H NMR (300 MHz, CDCl$_3$) 8.45 (1H, s), 8.02 (1H, s), 7.99 (2H, m), 7.47 (1H, t), 5.25 (2H, s), 3.15 (1H, tt), 2.10 (3H, s), 2.01 (2H, m), 1.84 (2H, m), 1.80 (6H, s), 1.75 (2H, m), 1.66 (9H, s), 1.58 (6H, s), 1.34 (4H, m).

Step k. 5-(Adamantan-1-yloxymethyl)-2-cyclohexyl-4-[4-(3-methoxycarbonyl-phenyl)-oxazol-2-yl]-imidazole. A solution of the product from step e above (330 mg, 0.54 mmol) in DCM (5 ml) containing excess diethylamine (3 ml) was stirred at room temperature for 30 h. The mixture was evaporated and purified by flash chromatography (Silica, DCM/ethyl acetate 3:1) to give 250 mg (90%) product. $^1$H NMR (300 MHz, CDCl$_3$) 10.0 (1H, br s), 8.44 (1H, s), 8.00 (2H, m), 7.98 (1H, s), 7.47 (1H, t), 5.07 (2H, s), 3.93 (3H, s), 2.70 (1H, m), 2.20 (3H, s), 1.91 (9H, m), 1.66 (10H, m), 1.22 (3H, m).

Step l. 3-{2-[5-(Adamantan-1-yloxymethyl)-2-cyclohexyl-1H-imidazol-4-yl]-oxazol-4-yl}-benzoic acid. A solution of lithium hydroxide (40 mg, 9.7 mmol) in water (3 ml) was added to a solution of the ester from step f above (250 mg, 0.48 mmol) in dioxan (7 ml) and the mixture stirred at room temperature overnight. The solvent was evaporated and the residue partitioned between ethyl acetate and water. The pH was adjusted to 5 with 1M HCl. The organic layer was separated, washed with water then brine, dried (Na$_2$SO$_4$) and evaporated. The crude product was triturated with ether to give 155 mg of acid. $^1$H NMR (300 MHz, d$_6$-DMSO) 13.00 (1H, br s), 12.22 (1H, s), 8.64 (1H, s), 8.54 (1H, s), 8.04 (1H, d), 7.88 (1H, d), 7.55 (1H, t), 4.87 (2H, s), 2.67 (1H, m), 2.11 (3H, m), 2.0–1.5 (6H, m), 1.81 (6H, s), 1.58 (6H, s), 1.31 (4H, m). The acid was converted to the N-methyl-D-glucamine salt and lyophilised from water/dioxan. Found: C, 60.49; H, 7.69; N, 7.62%. C$_{37}$H$_{52}$N$_4$O$_9$.2.1H$_2$O requires: C, 60.51; H, 7.71; N, 7.63%.

EXAMPLE 2

3-{2-[5-(2-Adamantan-1-yl-ethyl)-2-o-tolyl-1H-imidazol-4-yl]oxazol-4-yl}-benzoic acid 5-(2-Adamantan-1-ylethyl)-2-o-tolylimidazole-1,4-dicarboxylic acid 4-benzyl ester1-tert-butyl ester was prepared from 3-adamantan-1-yl-propionic acid and 2-methylbenzaldehyde following procedures similar to those described in Example 1 steps b–f. This was converted to the title compound using essentially the same procedures as Example 1 steps h–l. $^1$H NMR (300 MHz, d$_6$-DMSO) 13.10 (1H, br s), 12.52 (1H, s), 8.66 (1H, s), 8.47 (1H, s), 8.05 (1H, d), 7.88 (1H, d), 7.61 (1H, m), 7.55 (1H, t), 7.29 (3H, s), 3.09 (2H, m), 2.57 (3H, s), 1.98 (3H, s), 1.71 (6H, s), 1.61 (6H, s), 1.48 (2H, m). The acid was converted to the N-methyl-D-glucamine salt and lyophilised from water/dioxan. Found: C, 59.22; H, 7.60; N, 7.04%. C$_{39}$H$_{50}$N$_4$O$_8$.4.9H$_2$O requires: C, 59.18; H, 7.62; N, 7.08%.

EXAMPLE 3

Reaction Scheme 6

3-{2-[5-(Adamantan-1-yloxymethyl)-2-cyclohexyl-1H-imidazol-4-yl]-[1,2,4]oxadiazol-3-yl}-benzoic acid Step a. 3-(N-hydroxycarbamimidoyl)-benzoic acid benzyl ester. Hydroxylamine hydrochloride was reacted with 3-cyanobenzoic acid benzyl ester following the procedure described by J. A. Porco et al (Biorg. Med. Chem. Lett. 1999 9 209 note 10). $^1$H NMR (300 MHz, d$_6$-DMSO) 9.75 (1H, s), 8.31 (1H, s), 7.95 (2H, m), 7.43 (6H, m), 5.92 (2H, br s), 5.36 (2H, s).

Step b. 3-{2-[5-(Adamantan-1-yloxymethyl)-2-cyclohexyl-1H-imidazol-4-yl]-[1,2,4]oxadiazol-3-yl}-benzoic acid benzyl ester. A solution of the acid from Example 1, step f (2.56 g, 5.58 mmol) and 1,1'-carbonyldiimidazole (CDI) (0.99 g, 6.14 mmol) in dry DMF was stirred at room temperature for 1 h. The amidoxime from step a above (1.87 g, 6.14 mmol) was added and stirring continued overnight. A further portion of CDI (0.99 g, 6.14 mmol) was added and the mixture heated to 125° C. for 6 h. The solvent was removed in vacuo. The residue was taken up in DCM and washed with water (twice), 1M HCl, saturated sodium bicarbonate, and brine, dried (MgSO$_4$) and evaporated. Flash chromatography (Silica, DCM/ethyl acetate 85:15) yielded 808 mg (24%) product. $^1$H NMR (300 MHz, CDCl$_3$) 9.75 (1H, br s), 8.89 (1 h, s), 8.37 (1H, d), 8.21 (1H, d), 7.56 (1H, t), 7.45, 2H, m), 7.38 (3H, m), 5.41 (2H, s), 5.02 (2H, s), 2.79 (1H, tt), 2.20 (3H, s), 2.08 (2H, m), 1.86 (6H, s), 1.60 (6H, br s), 2.1–1.3 (10H, m).

Step c. 3-{2-[5-(Adamantan-1-yloxymethyl)-2-cyclohexyl-1H-imidazol-4-yl]-[1,2,4]oxadiazol-3-yl}-benzoic acid. 10% Palladium on charcoal (85 mg) was added to a solution of the product of the previous step (0.79 g, 1.33 mmol) in THF/methanol (1:1 mixture, 50 ml) and the mixture was stirred under an atmosphere of hydrogen for 3 h. The catalyst was removed by filtration and the filtrate evaporated to afford the product as a white solid (0.64 g, 95%). $^1$H NMR (300 MHz, d$_6$-DMSO) 13.20 (1H, br s), 12.63 (1H, s), 8.65 (1H, s), 8.28 (1H, d), 8.13 (1H, d), 7.72 (1H, t), 4.88 (2H, s), 2.72 (1H, t), 2.13 (3H, s), 1.93 (2H, m), 1.83 (6H, s), 1.8–1.5 (5H, m), 1.59 (6H, s), 1.32 (3H, m). The acid was converted to the N-methyl-D-glucamine salt and lyophilised from water/dioxan. Found: C, 58.96; H, 7.49; N, 9.46%. C$_{36}$H$_{51}$N$_5$O$_9$.2H$_2$O requires C, 58.99; H, 7.55; N, 9.56%.

EXAMPLE 4

3-{2-[5-(2-Adamantan-1-yl-ethyl)-2-cyclohexyl-1H-imidazol-4-yl]-[1,2,4]oxadiazol-3-3-yl}-benzoic acid This was prepared essentially as in Example 3 except that in step b the amidoxime was reacted with 5-(2-Adamantan-1-yl-ethyl)-2-cyclohexyl-imidazole-1,4-dicarboxylic acid 4-benzyl ester1-tert-butyl ester. $^1$H NMR (300 MHz, d$_4$-MeOH) 8.80 (1H, s), 8.33 (1H, d), 8.19 (1H, d), 7.64 (1H, t), 3.09 (2H, m), 2.78 (1H, tt), 2.01 (5H, m), 1.95–1.55 (17H, m), 1.43 (5H, m). The acid was converted to the N-methyl-D-glucamine salt and lyophilised from water/dioxan.

EXAMPLE 5

3-{2-[5-(2-Adamantan-1-yl-ethyl)-2-o-tolyl-1H-imidazol-4-yl]-[1,2,4]oxadiazol-3-yl}-benzoic acid This was prepared essentially as in Example 3 except that in step b the amidoxime was reacted with 5-(2-Adamantan-1-yl-ethyl)-2-o-tolyl-imidazole-1,4-dicarboxylic acid 4-benzyl ester1-tert-butyl ester. $^1$H NMR (300 MHz, d$_6$-DMSO) 8.67 (1H, s), 8.28 (1H, d), 8.13 (1H, d), 7.71 (1H, t), 7.62 (1H, d), 7.33 (3H, m), 3.11 (2H, m), 2.57 (3H, s), 1.98 (3H, br s), 1.67 (6H, s), 1.61 (6H, s), 1.47 (2H, m). The acid was converted to the N-methyl-D-glucamine salt and lyophilised from water/dioxan. Found: C, 61.64; H, 7.41; N, 9.61%. C$_{38}$H$_{49}$N$_5$O$_8$.2H$_2$O requires C, 61.54; H, 7.23; N, 9.44%.

EXAMPLE 6

Reaction Scheme 7

3-{2-[5-(Adamantan-1-yloxymethyl)-2-cyclohexyl-1H-imidazol-4-yl]-thiazol-4-yl}-benzoic acid Step a. 5-(Adamantan-1-yloxymethyl)-2-cyclohexyl-3H-imidazole-4-carboxylic acid. The benzyl ester from Example 1 step d was hydrogenolysed following the procedure described in Example 1 step f to give the corresponding acid.

Step b. 5-(Adamantan-1-yloxymethyl)-2-cyclohexyl-3H-imidazole-4-carboxylic acid amide. Oxalyl chloride (850 mg, 6.68 mmol) was added to a suspension of the acid from Example 1 step a above (1.6 g, 4.46 mmol) in DCM (20 ml) with two drops of DMF. The resulting solution was stirred at room temperature for 1 h then the solvent and excess oxalyl chloride were removed in vacuo. The residue was suspended in THF and ammonia was bubbled through for 10 min. The mixture was stirred at room temperature for 1.5 h then diluted with ethyl acetate and washed with water (2×30 ml), dried (MgSO$_4$) and evaporated to give a quantitative yield (1.64 g) of the title amide which was used without further purification. $^1$H NMR (300 MHz, d$_6$-DMSO) 11.90 (1H, br s), 6.97 (1H, br s), 6.85 (1H, br s), 4.73 (2H, s), 2.70 (1H, m), 2.09 (3H, br s), 1.82–1.24 (22H, m).

Step c. 5-(Adamantan-1-yloxymethyl)-2-cyclohexyl-3H-imidazole-4-carbothioic acid amide. Lawesson's reagent (0.66 g, 1.63 mmol) was added to a solution of the amide from step b (0.78 g, 2.2 mmol) in dimethoxyethane (DME) (10 ml) and the mixture was heated under reflux for 3 h. The solvent was evaporated, the residue taken up in ethyl acetate and washed with saturated aqueous sodium hydrogen carbonate (3×20 ml), brine (20 ml) then dried (MgSO$_4$). The crude product was purified by flash chromatography (Silica, DCM/ethyl acetate 95:5). Yield 0.53 g (64%). $^1$H NMR (300 MHz, CDCl$_3$) 9.95 and 9.75 (1H, 2×br s), 9.30 and 8.30 (1H, 2×br s), 7.29 and 7.00 (1H, 2×br s), 5.06 and 4.70 (2H, 2×s), 2.70 (1H, m), 2.18 (3H, br s), 2.03 (2H, m), 1.87–1.32 (20H, m).

Step d. 3-{2-[5-(Adamantan-1-yloxymethyl)-2-cyclohexyl-1H-imidazol-4-yl]-thiazol-4-yl}-benzoic acid methyl ester. 3-(2-Bromo-acetyl)-benzoic acid methyl ester was prepared as described by Schmied (Schmied, Gading, Monatshefte Chem. 1953, 84, 491). A solution of this bromoketone (0.44 g, 1.7 mmol) and the thioamide from step c (0.52 g, 1.4 mmol) in methanol (10 ml) was heated under reflux for 5 h. The solvent was evaporated and the residue taken up in ethyl acetate and washed with saturated aqueous sodium hydrogen carbonate (2×20 ml), brine (20 ml) then dried (MgSO$_4$). The crude product was purified by flash chromatography (Silica, DCM/ethyl acetate 95:5–90:10). Yield 0.36 g (48%). $^1$H NMR (300 MHz, CDCl$_3$) 9.25 (1H, br s), 8.64 (1H, s), 8.16 (1H, d), 8.01 (1H, d), 7.51 (2H, m), 5.17 (2H, s), 3.95 (3H, s), 2.79 (1H, m), 2.20 (3H, br s), 2.07 (2H, m), 1.90–1.36 (20H, m).

Step e. 3-{2-[5-(Adamantan-1-yloxymethyl)-2-cyclohexyl-1H-imidazol-4-yl]-thiazol-4-yl}-benzoic acid. To a solution of the methyl ester from step d above (0.35 g, 0.66 mmol) in THF/H$_2$O (10 ml/5 ml) was added lithium hydroxide monohydrate (0.113 g, 2.7 mmol) and the mixture was heated under reflux for 4 h. The THF was evaporated and the pH adjusted with 1M HCl to pH=5. The product was extracted with ethyl acetate and the organic phase washed with brine, dried and evaporated. The crude product was purified by flash chromatography (Silica, DCM/methanol 95:5). Yield 0.30 g (88%). $^1$H NMR (300 MHz, d$_6$-DMSO) 13.00 (12H, br s), 12.16 (1H, s), 8.63 (1H, s), 8.21 (1H, d), 8.02 (1H, s), 7.90 (1H, d), 7.55 (1H, t), 4.99 (2H, s), 2.67 (1H, m), 2.08 (3H, m), 1.93–1.51 (18H, m), 1.35–1.25 (4H, m). The acid was converted to the N-methyl-D-glucamine salt and lyophilised from water/dioxan. Found: C, 59.62; H, 7.61; N, 7.31%. C$_{37}$H$_{52}$N$_4$O$_8$S.1.9H$_2$O requires C, 59.48; H, 7.53; N, 7.50%.

EXAMPLE 7

Reaction Scheme 8

3-[5'-(Adamantan-1-yloxymethyl)-2'cyclohexyl-1H, 1H'-[2,4']biimidazolyl-4-yl]-benzoic acid Step a. 3-Acetylbenzoic acid. 3-Acetylbenzonitrile (2.32 g, 16 mmol) was heated under reflux in 6M hydrochloric acid (25 ml) for 7 h. The mixture was cooled and the precipitate filtered, washed with water, and dried in vacuo. Yield 2.36 g (90%). $^1$H NMR (300 MHz, DMSO) 13.25 (1H, br s), 8.44 (1H, s), 8.18 (2H, m), 7.66 (1H, t), 2.62 (3H, s).

Step b. 3-Acetylbenzoic acid methyl ester. A solution of the acid from step a (2.36 g, 14.4 mmol) in methanol (25 ml) containing concentrated hydrochloric acid (2 ml) was heated under reflux for 8 h. The solvent was evaporated and the residue taken up in ethyl acetate and washed with saturated sodium bicarbonate solution until the washings were basic (3 times), water and brine, dried (MgSO$_4$) and evaporated. Yield 2.40 g (94%). $^1$H NMR (300 MHz, CDCl$_3$) 8.60 (1H, s), 8.25 (1H, d), 8.16 (1H, d), 7.57 (1H, t), 3.97 (3H, s), 2.66 (3H, s).

Step c. 3-(2,2-Dibromo-acetyl)-benzoic acid methyl ester. A solution of bromine (1.72 ml, 33.4 mmol) in chloroform (10 ml) was added dropwise to a solution of the ketoester from step b (2.40 g, 13.5 mmol) in chloroform (25 ml) at room temperature. The mixture was stirred overnight then washed with 5% sodium thiosulphate solution, water and brine, dried MgSO$_4$), and evaporated. The crude product was purified by flash chromatography (silica, diethyl ether/hexane 3:7). Yield 3.73 g (73%). $^1$H NMR (300 MHz, CDCl$_3$) 8.72 (1H, s), 8.32 (1H, d), 8.29 (1H, d), 7.62 (1H, t), 6.72 (1H, s), 3.98 (3H, s).

Step d. 5-(Adamantan-1-yloxymethyl)-1-benzyl-2-cyclohexyl-1H-imidazole-4-carboxylic acid benzyl ester. To a solution of the product of example 1, step d (2.1 g, 4.69 mmol) in DMF (15 ml) was added sodium hydride (60% dispersion in mineral oil, 225 mg, 5.62 mmol). The mixture was stirred at ambient temperature for 0.5 h then benzyl bromide (0.67 ml, 5.62 mmol) was added. The reaction mixture was stirred at ambient temperature for 16 h, then partitioned between ethyl acetate and water. The organic layer was washed with 1M HCl, saturated sodium hydrogencarbonate, and brine, dried (MgSO$_4$) and evaporated. The major isomer was isolated by flash chromatography (silica, DCM/ethyl acetate 92:8) (2.15 g, 85%). $^1$H NMR (300 MHz, CDCl$_3$) 7.45 (2H, dd), 7.37–7.27 (6H, m), 6.98 (2H, m), 5.37 (2H, s), 5.28 (2H, s), 4.68 (2H, s), 2.52 (1H, m), 2.14 (2H, br s), 2.04 (3H, br s), 1.78–1.35 (17H, m), 1.28–1.14 (3H, m).

Step e. [5-(Adamantan-1-yloxymethyl)-1-benzyl-2-cyclohexyl-1H-imidazole-4-yl]-methanol Lithium aluminium hydride (300 mg, 8.20 mmol) was added in small portions to an ice cooled solution of the product of step d (2.20 g, 4.10 mmol) in THF (25 ml). The suspension was allowed to warm to ambient temperature and stirred for 2 h. The reaction mixture was cooled with ice and sodium hydroxide solution (2N, 1.6 ml) was slowly added. The reaction mixture was diluted with ethyl acetate (50 ml) and filtered through a plug of Celite and MgSO$_4$. The filtrate was evaporated under reduced pressure and the residue was crystallised from diethyl ether to afford white crystals (1.40 g, 79%). $^1$H NMR (300 MHz, CDCl$_3$) 7.28 (3H, m), 7.00 (2H, m), 5.18 (2H, s), 4.63 (2H, d), 4.34 (2H, s), 2.64 (1H, br m), 2.50 (1H, m), 2.13 (3H, br s), 1.72–1.54 (19H, m), 1.25 (3H, m).

Step f. 5-(Adamantan-1-yloxymethyl)-1-benzyl-2-cyclohexyl-1H-imidazole-4-carbaldehyde. To a solution of the product of step e (1.40 g, 3.22 mmol) in dioxane (40 ml) was added manganese(IV) oxide (1.45 g, 16.7 mmol) and the mixture was stirred at ambient temperature for 3 h. The reaction mixture was filtered through Celite and the filtrate was evaporated to afford colourless foam (1.38 g, 99%). $^1$H NMR (300 MHz, CDCl$_3$) 9.99 (1H, s), 7.32 (3H, m), 7.00 (2H, d), 5.31 (2H, s), 4.74 (2H, s), 2.51 (1H, m), 2.13 (3H, br s), 1.78–1.57 (19H, m), 1.22 (3H, m).

Step g. 3-[5'-(Adamantan-1-yloxymethyl)-1'-benzyl-2'-cyclohexyl-1H,1H'-[2,4']biimidazolyl-4-yl]-benzoic acid methyl ester. A solution of the dibromoketone from step c (330 mg, 0.98 mmol) and the aldehyde from the previous step (345 mg, 0.8 mmol) in methanol saturated with ammonia (10 ml) was stirred at room temperature for 24 h. The solvent was evaporated and the residue purified by flash chromatography (Silica, hexane/ethyl acetate 55:45) to give 130 mg (27%) product. $^1$H NMR (300 MHz, CDCl$_3$) 11.50 (1H, br), 8.49 (1H, s), 8.06 (1H, d), 7.87 (1H, d), 7.42 (1H, t), 7.33 (4H, m), 7.06 (2H, m), 5.33 (2H, s), 3.91 (3H, s), 2.50 (1H, m), 2.14 (3H, s), 1.85 (5H, s), 1.61 (14H, m) 1.14 (3H, m).

Step i. 3-[5'-(Adamantan-1-yloxymethyl)-2'-cyclohexyl-1H,1H'-[2,4']biimidazolyl-4-yl]-benzoic acid methyl ester. 10% Palladium on charcoal (9 mg) was added to a solution of the product of the previous step (80 mg, 0.13 mmol) in glacial acetic acid (5 ml) and the mixture was stirred under an atmosphere of hydrogen for 5 h. The mixture was filtered and evaporated. The residue was taken up in ethyl acetate and washed with saturated sodium bicarbonate solution (3 times), brine, dried (MgSO$_4$) and evaporated. The crude product was purified by flash chromatography (silica, 8% methanol/92% DCM). Yield 35 mg (53%). $^1$H NMR (300 MHz, CDCl$_3$) 8.41 (1H, br s), 8.28 (1H, d), 7.90 (2H, m), 7.45 (1H, t), 7.38 (1H, s), 4.83 (2H, br s), 3.93 (3H, s), 2.67 (1H, m), 2.19 (3H, s), 2.04–1.32 (22H, m).

Step j. 3-[5'-(Adamantan-1-yloxymethyl)-2'-cyclohexyl-1H,1H'-[2,4]biimidazolyl-4-yl]-benzoic acid. An aqueous solution of potassium hydroxide (150 mg in 0.5 ml) was added to a solution of the ester from step i above (98 mg, 0.19 mmol) in ethanol (9 ml) and the mixture heated under reflux for 45 min. The ethanol was evaporated and the residue partitioned between ethyl acetate and water. The pH was adjusted to pH=5 with 1M HCl. The organic layer was separated, washed with brine, dried (Na2SO4) and evaporated. The crude product was crystallised from methanol. Yield 38 mg (40%). $^1$H NMR (300 MHz, DMSO) 12.75 (1H, br), 12.05 (1H, br s), 11.90 (1H, br s), 8.47 (1H, s), 8.10 (1H, d), 7.73 (1H, d), 7.54 (1H, s), 7.43 (1H, t), 4.96 (2H, s), 2.64 (1H, m), 2.10 (3H, s), 1.95–1.50 (18H, m), 1.25 (4H, m). The acid was converted to the N-methyl-D-glucamine salt and lyophilised from water/dioxan. Found: C, 57.85; H, 8.04; N, 8.89%. C$_{37}$H$_{53}$N$_5$O$_8$.4.1H$_2$O requires C, 57.67; H, 8.02; N, 9.09%.

EXAMPLE 8

Reaction Scheme 1

3-{5-[5-(Adamantan-1-yloxymethyl)-2-cyclohexyl-1H-imidazol-4-yl]-[1,3,4]thiadiazol-2-yl}-benzoic acid Step a. 5-(Adamantan-1-yloxymethyl)-2-cyclohexyl-1H-imidazole-4-carboxylic acid hydrazide. A suspension of 5-(Adamantan-1-yloxymethyl)-2-cyclohexyl-1H-imidazole-4-carboxylic acid (2.10 g, 6.0 mmol.), EDC (1.27 g, 6.6 mmol), and HOBt (1.01 g, 6.6 mmol), in DMF (60 ml) was stirred at room temperature for 1 h to give a clear solution of the active ester. 1.0M anhydrous hydrazine in THF solution (12 ml, 12 mmol) was added and stirring was continued for 2 hr. The solution was diluted with ethyl acetate (150 ml) and washed with four times with water (100 ml). The solution was dried over anhydrous magnesium sulphate and evaporated to afford the product (2.12 g, 97%). $^1$H NMR (D$_6$ DMSO) 12.00 (1H, br.s), 8.50 (1H, br. s), 4.70 (2H, s), 3.40 (2H br, s), 2.63 (1H, m), 1.98 (3H, s), 1.82–1.24 (22H, m).

Step b. 3-{N$^1$-[5-(Adamantan-1-yloxymethyl)-2-cyclohexyl-1H-imidazole-4-carbonyl]-hydrazinocarbonyl}-benzoic acid methyl ester. A solution of 5-(Adamantan-1-yloxymethyl)-2-cyclohexyl-1H-imidazole-4-carboxylic acid hydrazide. (744 mg, 2 mmol), isophthalic acid mono methyl ester (396 mg, 2.2 mmol), EDC (422 mg, 2.2 mmol), and HOBt (337 mg, 2.2 mmol), in DMF (10 ml) was stirred at room temperature for 16 hr. The reaction mixture was partitioned between ethyl acetate (50 ml) and water (50 ml). The organic layer was washed successively with 5% sodium bicarbonate (40 ml), water (40 ml), brine (40 ml), dried over anhydrous magnesium sulphate and evaporated to afford the product. (914 mg, 86%). $^1$H NMR (D$_6$ DMSO) 12.11 (1H, s), 10.54 (1H, s), 9.48 (1H, s), 8.49 (1H, s), 8.15 (2H, d), 7.67 (1H, t) 4.74 (2H, s), 3.90 (3H, s), 2.67 (1H, m), 2.09 (3H, s), 1.88–1.23 (22H, m).

Step c. 3-{5-[5-(Adamantan-1-yloxymethyl)-2-cyclohexyl-1H-imidazol-4-yl]-[1,3,4]thiadiazol-2-yl}-benzoic acid methyl ester. A solution of 3-{N$^1$-[5-(Adamantan-1-yloxymethyl)-2-cyclohexyl-1H-imidazole-4-carbonyl]-hydrazinocarbonyl}-benzoic acid methyl ester (254 mg, 1 mmol) and Lawesson's reagent (506 mg, 1.25 mmol) in THF (10 ml) was stirred and refluxed under dry argon atmosphere for 6 hr. The solution was diluted with ethyl acetate (20 ml) and washed with two portions of saturated sodium bicarbonate (20 ml). The organic layer was dried over anhydrous magnesium sulphate and evaporated. The residue was subjected to flash column chromatography on silica eluting with DCM/methanol (19:1) to afford the product. (110 mg, 21%). $^1$H NMR (D$_6$ DMSO) 12.33 (1H, s), 8.54 (1H, s), 8.23 (1H, d), 8.10 (1H, d) 7.71 (1H, t), 4.88 (2H, s) 3.91 (3H, s), 2.70 (1H, m), 1.90 (3H, s), 1.80–1.28 (22H, m).

Step d. 3-{5-[5-(Adamantan-1-yloxymethyl)-2-cyclohexyl-1H-imidazol-4-yl]-[1,3,4]thiadiazol-2-yl}-benzoic acid. A solution of 3-{5-[5-(Adamantan-1-yloxymethyl)-2-cyclohexyl-1H-imidazol-4-yl]-[1,3,4]thiadiazol-2-yl}-benzoic acid methyl ester (100 mg, 0.187 mmol) and 0.1M sodium hydroxide (3 ml, 0.3 mmol) in ethanol (10 ml) was stirred and refluxed for 1 hr. The solution was acidified to pH 4 with 1M phosphoric acid (0.3 ml), evaporated to low volume and partitioned between water (20 ml) and ethyl acetate (20 ml). The organic layer was dried over anhydrous magnesium sulphate and evaporated to afford the product (89 mg, 92%) H NMR (D$_6$ DMSO) 13.20 (1H, br. s), 12.25 (1H, br. s), 8.51 (1H, s), 8.20 (1H, d), 8.09 (1H, d), 7.68 (1H, t), 4.88 (2H, s), 2.70 (1H, m), 2.12 (3H, s) 1.90–1.27 (22H, m). The acid was converted to the N-Methyl-D-glucamine salt and lyophilised from water/dioxan. Found: C, 57.69; H, 7.60; N, 9.48%; C$_{36}$H$_{51}$N$_5$O$_8$S.2H$_2$O requires: C, 57.65; H, 7.39; N, 9.34%.

EXAMPLE 9

Reaction Scheme 1

3-{5-[5-(Adamantan-1-yloxymethyl)-2-cyclohexyl-1H-imidazol-4-yl]-[1,3,4]oxadiazol-2-yl}-benzoic acid Step a. 3-{5-[5-(Adamantan-1-yloxymethyl)-2-cyclohexyl-1H-imidazol-4-yl]-[1,3,4]oxadiazol-2-yl}-benzoic acid methyl ester. A solution of 3-{N$^1$-[5-(Adamantan-1-yloxymethyl)-2-cyclohexyl-1H-imidazole-4-carbonyl]-hydrazinocarbonyl}-benzoic acid methyl ester (360 mg, 0.674 mmol), triphenylphosphine (262 mg, 1 mmol) and 1,8-diazabicyclo[5.4.0]undec-7-ene (DBU) (298 ul, 2 mmol) in acetonitrile (5 ml) and carbon tetrachloride (3 ml) was stirred at room temperature for 4 hr. The solution was then evaporated and the residue subjected to flash column chromatography on silica, eluting with DCM/ethyl acetate (7:3) to afford the product. (224 mg, 64%). $^1$H NMR (D$_6$DMSO) 12.41 (1H, br.s), 8.52 (1H, s), 8.30 (1H, d), 8.17 (1H, d) 7.77 (1H, t), 4.80 (2H, s), 3.92 (3H, s), 2.73 (1H, m), 2.11 (3H, s), 1.90–1.28 (22H, m).

Step b. 3-{5-[5-(Adamantan-1-yloxymethyl)-2-cyclohexyl-1H-imidazol-4-yl]-[1,3,4]oxadiazol-2-yl}-benzoic acid. The title compound was prepared in 90% yield using essentially the same procedure as in Example 1d, but using 3-{5-[5-(Adamantan-1-yloxymethyl)-2-cyclohexyl-1H-imidazol-4-yl]-[1,3,4]oxadiazol-2-yl}-benzoic acid methyl ester instead of 3-{5-[5-(Adamantan-1-yloxymethyl)-2-cyclohexyl-1H-imidazol-4-yl]-[1,3,4]thiadiazol-2-yl}-benzoic acid methyl ester. H NM.R. (D$_6$ DMSO) 13.30 (1H, br s), 12.50 (1H, br s), 8.53 (1H, s), 8.30 (1H, d), 8.17 (1H, d), 7.75 (1H, t), 4.79 (2H, s), 2.74 (1H, m), 2.11 (3H, s), 1.90–1.29 (22H, m). The acid was converted to the N-Methyl-D-glucamine salt and lyophilised from water/dioxan. Found: C, 58.92; H, 7.77; N, 9.39%; C$_{36}$H$_{51}$N$_5$O$_9$.2H$_2$O requires: C, 58.92; H, 7.55; N, 9.54%.

EXAMPLE 10

Reaction Scheme 2

3-{5-[5-(Adamantan-1-yloxymethyl)-2-cyclohexyl-1H-imidazol-4-yl]-[1,3,4]triazol-3-yl}-benzoic acid Step a. 3-({[5-(Adamantan-1-yloxymethyl)-2-cyclohexyl-1H-imidazole-4-carbonyl]-hydrazono}-amino-methyl)-benzoic acid benzyl ester. A solution of 5-(Adamantan-1-yloxymethyl)-2-cyclohexyl-1H-imidazole-4-carboxylic acid hydrazide (278 mg, 0.774 mmol), 3-Methoxycarbonimidoyl-benzoic acid benzyl ester hydrochloride (305 mg, 1 mmol), triethylamine (280 μL, 2 mmol) in ethanol (6 mL) was stirred and refluxed for 5 hr. The solution was evaporated and the residue subjected to flash column chromatography on silica, eluting with DCM/methanol (19:1) to afford the product. (170 mg, 36%). $^1$H NMR (D$_6$DMSO) 12.04 (1H, s), 9.50 (1H, s), 8.47 (1H, s), 8.05 (2H, m), 7.57 (1H, t), 7.47–7.30 (5H, m), 6.68 (2H, br. s), 5.38 (2H, s), 4.76 (2H, s), 2.66 (1H, m), 2.10 (3H, s), 1.91–1.23 (22H, m).

Step b. 3-{5-[5-(Adamantan-1-yloxymethyl)-2-cyclohexyl-1H-imidazol-4-yl]-[1,3,4]triazol-3-yl}-benzoic acid benzyl ester. A solution of 3-({[5-(Adamantan-1-yloxymethyl)-2-cyclohexyl-1H-imidazole-4-carbonyl]-hydrazono}-amino-methyl)-benzoic acid benzyl ester (360 mg, 0.674 mmol), triphenylphosphine, (262 mg, 1 mmol) and DBU (298 μL, 2 mmol) in acetonitrile (5 mL) and carbon tetrachloride (3 mL) was stirred at room temperature for 16 hr. The solution was evaporated and the residue subjected to flash column chromatography on silica, eluting with DCM/ethyl acetate (7:3) to afford the product. (100 mg, 29%). $^1$H NMR (D$_6$ DMSO) 12.17 (2H, br s), 8.69 (1H, s), 8.30 (1H, d), 7.10 (1H, m), 7.99 (1H, d) 7.45 (5H, m), 5.39 (2H, s), 4.94 (2H, s), 2.70 (1H, m), 2.06 (3H, s), 1.89–1.27 (22H, m).

Step c. 3-{5-[5-(Adamantan-1-yloxymethyl)-2-cyclohexyl-1H-imidazol-4-yl]-[1,3,4]triazol-3-yl}-benzoic acid. A solution of 3-{5-[5-(Adamantan-1-yloxymethyl)-2-cyclohexyl-1H-imidazol-4-yl]-[1,3,4]triazol-3-yl}-benzoic acid benzyl ester (100 mg, 0.194 mmol) in methanol/THF (1:1, 20 ml) was hydrogenated over 10% palladium on carbon catalyst (10 mg) at room temperature and pressure for 2 hr. The catalyst was removed by filtration through a pad of celite and the filtrate was evaporated to afford the product. (75 mg, 93%). $^1$H NMR (D$_6$ DMSO) 12.16 (1H, br s), 8.67 (1H, s), 8.21 (1H, d), 7.94 (1H, d), 7.55 (1H, t), 4.95 (2H, s), 2.70 (1H, m), 2.11 (3H, s), 1.94–1.24 (22H, m). The acid was converted to the N-Methyl-D-glucamine salt and lyophilised from water/dioxan. Found: C, 57.78; H, 7.89; N, 11.03%; C$_{36}$H$_{52}$N$_6$O$_8$. 3H$_2$O requires: C, 57.58; H, 7.79; H, 11.19%.

EXAMPLE 11

Reaction Scheme 3

3-{2-[5-(Adamantan-1-yloxymethyl)-2-cyclohexyl-1H-imidazol-4-yl]-4,5-dihydro-oxazol-5-yl}-benzoic acid Step a. 3-Formyl benzoic acid methyl ester. A solution of 3-formyl benzoic acid (2.0 g, 13.33 mmol) in methanol (30 ml) was saturated with dry hydrogen chloride gas, then stirred and refluxed for 3 hr. The solution was poured onto water (50 ml) and stirred for 30 min, then diluted with further water (20 ml). The white precipitate formed was filtered off, washed with water and dried to afford the product (1.77 g, 81%). $^1$H NMR (CDCl$_3$) 10.07 (1H, s), 8.52 (1H, s), 8.30 (1H, d), 8.09 (1H, d), 7.60 (1H, t), 3.97 (3H, s).

Step b. 3-(2-nitro-1-hydroxyethyl)-benzoic acid methyl ester. To a solution of 3-formyl benzoic acid methyl ester (1.77 g, 10.79 mmol) in ethanol (18 ml), water (2 ml) and nitromethane (2 ml) was added 5 drops of piperidine and 5 drops of acetic acid. The solution was stood for 24 h then evaporated. The residue was taken up in ethyl acetate (40 ml) and the solution washed succesively with 2M hydrochloric acid (20 ml), water (20 ml), 5% sodium carbonate (20 ml), brine (20 ml) dried over anhydrous magnesium sulphate and evaporated. The residue was subjected to flash column chromatography on silica, eluting with DCM/ethyl acetate (9:1) to afford the product as a pale yellow oil. (1.33 g, 55%). $^1$H NMR (CDCl$_3$) 8.09 (1H, s), 8.08 (1H, d), 7.63 (1H, d), 7.52 (1H, t), 5.23 (1H, m), 4.58 (2H, m), 3.94 (3H, s), 3.02 (1H, d).

Step c. 3-(3-amino-1-hydroxyethyl)-benzoic acid methyl ester. A solution of 3-(2-nitro-1-hydroxyethyl)-benzoic acid methyl ester (1.33 g, 5.91 mmol) in ethanol (30 ml) was hydrogenated at room temperature and pressure over platinum oxide catalyst (100 mg) for 6 hr. The catalyst was removed by filtration through a pad of celite. The filtrate was evaporated to afford the product as a colourless oil (1.10 g, 96%). $^1$H NMR (CDCl$_3$) 8.03 (1H, s), 7.94 (1H, d), 7.57 (1H, d), 7.43 (1H, t), 4.69 (1H, m), 3.92 (3H, s) 3.02 (1H, dd), 2.80 (1H, dd) 2.20 (2H, brs).

Step d. 3-(2-{[5-(Adamantan-1-yloxymethyl)-2-cyclohexyl-1H-imidazole-4-carbonyl]-amio}-1-hydroxyethyl)-benzoic acid methyl ester. A solution of 5-(Adamantan-1-yloxymethyl)-3-t-butoxycarbonyl-2-cyclohexyl-1H-imidazole-4-carboxylic acid (2.29 g, 5 mmol), 3-(3-amino-1-hydroxyethyl)-benzoic acid methyl ester (1.10 g, 5.61 mmol), HOBt (0.94 g, 5.5 mmol), EDC (1.06 g, 5.5 mmol) and DMAP (20 mg) in DMF (25 ml) was stirred at room temperature for 72 h. The reaction mixture was partitioned between water (70 ml) and ethyl acetate (70 ml). The organic layer was washed with water (3×50 ml), dried over anhydrous magnesium sulphate, and evaporated. The residual solid was recrystallised from ethyl acetate/hexane (1:1) to afford the product as white crystals. (1.09 g, 41%). $^1$H NMR (D$_6$ DMSO) 11.96 (1H, br.s), 7.99 (1H, s), 7.84 (1H, d), 7.64 (1H, s), 7.63 (1H, d), 7.46 (1H, t), 5.74 (1H, d), 4.78 (1H, m), 4.76 (2H, s), 3.84 (3H, s), 3.53 (1H, m), 3.25 (2H, m), 2.61 (1H, m), 2.09 (3H, s), 1.87–1.24 (22H, m).

Step e. 3-{2-[5-(Adamantan-1-yloxymethyl)-2-cyclohexyl-1H-imidazol-4-yl]4,5-dihydro-oxazol-5-yl}-benzoic acid methyl ester. A solution of 3-(2-{[5-(Adamantan-1-yloxymethyl)-2-cyclohexyl-1H-imidazole-4-carbonyl]-amino}-1-hydroxy-ethyl)-benzoic acid methyl ester (535 mg, 1 mmol), triphenylphospine (760 mg, 2.9 mmol), and diisopropylethylamine (540 ul, 3.1 mmol), in acetonitrile (10 ml) and carbon tetrachloride (5 ml) was stirred at room temperature for 3 hr. The solution was diluted with DCM (40 ml), washed with saturated sodium bicarbonate (40 ml), and brine (40 ml), dried over anydrous magnesium sulphate, and evaporated. The residue was subjected to flash column chromatography on silica, eluting with DCM/methanol (19:1) to afford the product mixed with triphenylphosphine oxide from which it was inseparable (870 mg). $^1$H NMR (CDCl$_3$) 9.50 (1H, br.s), 8.04 (1H, s), 7.91 (1H, d), 7.73 (1H, d), 7.50 (1H, t), 5.62 (1H, t), 4.82 (2H, s), 4.45 (1H, m), 3.91 (4H, s+m), 2.75 (1H, m), 2.11–1.21 (25H, m) (also shows presence of triphenyl phosphine oxide).

Step f. 3-{2-[5-(Adamantan-1-yloxymethyl)-2-cyclohexyl-1H-imidazol-4-yl]-4,5-dihydro-oxazol-5-yl}-benzoic acid. A solution of 3-{2-[5-(Adamantan-1-yloxymethyl)-2-cyclohexyl-1H-imidazol-4-yl]-4,5-dihydro-oxazol-5-yl}-benzoic acid methyl ester (870 mg, also contains triphenylphosphine oxide) and 1M lithium hydroxide (1 ml) in methanol (9 ml) was stirred and refluxed for 1 h. the solution was cooled, acidified to pH 4 with 1M phosphoric acid (1 ml), then evaporated to low volume and partitioned between ethyl acetate (20 ml) and brine (20 ml). The organic layer was dried over anhydrous magnesium sulphate and evaporated. The residue was subjected to flash column chromatography on silica, eluting with DCM/methanol (9:1), to afford the product. (95 mg). It was converted to the hydrochloride salt and recrystallised from ethanol/ether. $^1$H NMR (D$_6$ DMSO) 8.74 (1H, br s), 8.04 (1H, s), 7.92 (1H, d), 7.74 (1H, d), 7.53 (1H, t), 5.35 (1H, t), 4.68 (1H, s), 3.88 (2H, m), 2.91 (1H, m), 1.93 (3H, s), 1.80–1.25 (22H, m). Found: C, 58.01; H, 7.04; N, 6.76%; C$_{30}$H$_{39}$Cl$_2$N$_3$O$_4$. 2.5H$_2$O requires: C, 57.96; H, 7.14; N, 6.67%.

EXAMPLE 12

6-{5-[5-(Adamantan-1-yloxymethyl)-2-cyclohexyl-1H-imidazol-4-yl]-[1,3,4]oxadiazol-2-yl}-pyridine-2-carboxylic acid The title compound was prepared using essentially the same procedure as in Example 8, step b. with the modification that pyridine-2,6-dicarboxylic acid mono methyl ester was used instead of isophthalic acid mono methyl ester, then following the procedure for example 2. $^1$H NMR (D$_6$ DMSO) 13.50 (1H, br.s), 12.40 (11H, br.s), 8.39 (1H, m), 8.20 (2H, m), 4.83 (2H, s), 2.75 (1H, m), 2.10 (3H, s) 1.88–1.30 (22H, m). The acid was converted to the N-Methyl-D-glucamine salt and lyophilised from water/dioxan. Found: C, 56.60; H, 7.71; N, 11.33%; C$_{35}$H$_{50}$N$_6$O$_9$.2.5H$_2$O requires: C, 56.51; H, 7.45; N, 11.30%.

EXAMPLE 13

5-{5-[5-(Adamantan-1-yloxymethyl)-2-cyclohexyl-1H-imidazol-4-yl]-[1,3,4]oxadiazo-2-yl}-nicotinic acid The title compound was prepared according to the procedure in Example 12 with the modification that pyridine-3,5-dicarboxylic acid mono methyl ester was used instead of pyridine-2,6-dicarboxylic acid mono methyl ester. $^1$H NMR (D$_6$ DMSO) 12.50 (2H, br s), 9.40 (1H, s), 9.23 (1H, s), 8.72 (1H, s), 4.79 (2H, s), 2.78 (1H, m), 2.11 (3H, s), 1.91–1.28 (22H, m). The acid was converted to the N-Methyl-D-glucamine salt and lyophilised from water/dioxan. Found: C, 57.59; H, 7.62; N, 11.43; C$_{35}$H$_{50}$N$_6$O$_9$.1.5H$_2$O requires: C, 57.92; H, 7.36; N, 11.57%.

EXAMPLE 14

2-{5-[5-(Adamantan-1-yloxymethyl)-2-cyclohexyl-1H-imidazol-2-yl]-[1,3,4]oxadiazol-2-yl}-isonicotinic acid. (*** regiosomerism not absolutely assigned)

The title compound was prepared according to the procedure in Example 5 with the modification that pyridine-2,4-dicarboxylic acid-4 mono methyl ester was used instead of pyridine-2,6-dicarboxylic acid mono methyl ester. $^1$H NMR (D$_6$ DMSO) 14.00 (1H, br s), 12.45 (1H, br s), 8.95 (1H, d), 8.51 (1H, s), 8.02 (1H, d), 4.81 (2H, s), 2.74 (1H, m),1.98 (3H, s), 1.80–1.29 (22H, m). The acid was converted to the N-Methyl-D-glucamine salt and lyophilised from water/dioxan. Found: C, 58.17; H, 7.59; N, 11.22%; C$_{35}$H$_{50}$N$_6$O$_9$.5H$_2$O requires: C, 57.92; H, 7.36; N, 11.57%.

EXAMPLE 15

4-{5-[5-(Adamant-1-yloxymethyl)-2-cyclohexyl-1H-imidazol-2-yl]-[1,3,4]oxadiazol-2-yl}-benzoic acid The title compound was prepared according to the procedure in Example 8, step b, with the modification that terephthalic acid mono methyl ester was used instead of isophthalic acid mono methyl ester, then following the procedure for example 9. $^1$H NMR (D$_6$ DMSO) 13.5–13.00 (2H, br s), 8.15 (4H, s), 4.80 (2H, s), 2.76 (1H, m), 2.11 (3H, s), 1.97–1.30 (22H, m). The acid was converted to the N-Methyl-D-glucamine salt and lyophilised from water/dioxan. Found: C, 60.39; H, 7.69; N, 9.82%. C$_{36}$H$_{51}$N$_5$O$_9$.H$_2$O Requires: C, 60.40; H, 7.46; N, 9.78%.

EXAMPLE 16

3-{5-[5-(Adamantan-1-yloxymethyl)-2-bicyclo[2.2.2]oct-1-yl-1H-imidazol-4-yl]-[1,3,4]oxadiazol-2-yl}-benzoic acid The title compound was prepared according to the procedure in Example 8, step a, with the modification that 5-(Adamantan-1-yloxymethyl)-2-bicyclo[2.2.2]oct-1-yl-1H-imidazole-4-carboxylic acid was used instead of 5-(Adamantan-1-yloxymethyl)-2-cyclohexyl-1H-imidazole-4-carboxylic acid, then following the procedure for example 9. $^1$H NMR (D$_6$ DMSO) 12.50 (1H, brs), 8.54 (1H, s), 8.30 (1H, d), 8.17 (1H, d), 7.75 (1H, t), 4.77 (2H, s), 2.10 (3H, s), 1.97–1.53 (25H, m). The acid was converted to the N-Methyl-D-glucamine salt and lyophilised from water/dioxan. Found: C, 58.68; H, 7.84; N, 9.05%. C$_{38}$H$_{53}$N$_5$O$_9$.3H$_2$O Requires: C, 58.67; H, 7.65; N, 9.00%.

EXAMPLE 17

Reaction Scheme 4

3-{5-[5-(Adamantan-1-yloxymethyl)-2-cyclohexyl-3-hydroxy-1H-imidazol-4-yl]-[1,3,4]oxadiazol-2-yl}-benzoic acid Step a. 5-[2-(Adamantan-1-yloxy)-1-hydroxy-ethylidene]-2,2-dimethyl-[1,3]dioxane-4,6-dione. A mixture of (Adamantan-1-yloxy)-acetic acid (32.3 g, 0.153 mol) and CDI (27.6 g, 0.17 mol) in anhydrous DCM (600 ml) was stirred at 0° C. for 15 min., then at room temperature for 75 min. The mixture was concentrated in vacuo to half volume and the solution added dropwise over 20 min. to a solution of 2,2-dimethyl-1,3-dioxan-4,6-dione (Meldrum's acid, 22.1 g, 0.153 mol) and pyridine (30 ml, 0.371 mol) in anhydrous DCM (450 ml) at 0° C. under dry argon. The mixture was allowed to warm up to room temperature and stirred for 16 h. The solution was washed with 2M HCl (2×500 ml), brine (500 ml), and dried (MgSO$_4$). Filtration and evaporation gave a white solid which was washed with hexane and dried to afford the product. (50.1 g, 97%). $^1$H NMR (CDCl$_3$) 4.92 (2H, s), 2.19 (3H brs), 1.82–1.59 (12H, m), 1.74 (6H, s).

Step b. 4-(Adamantan-1-yloxy)-3-oxo-butyric acid benzyl ester. A mixture of 5-[2-(Adamantan-1-yloxy)-1-hydroxy-ethylidene]-2,2-dimethyl-[1,3]dioxane-4,6-dione. (5.70 g 16.9 mmol) and benzyl alcohol (1.75 ml, 16.9 mmol) in toluene (75 ml) was refluxed for 3 hr.

The mixture was cooled and evaporated in vacuo and the residue purified by flash column chromatography on silica eluting with DCM/ethylacetate (98:2) to afford the product as a colourless oil. (4.26 g, 74%). $^1$H NMR (CDCl$_3$) 7.36 (5H, m), 5.19 (2H, s), 4.05 (2H, s), 3.63 (2H, s), 2.14 (3H, br.s), 1.76–1.55 (12H, m).

Step c. 4-(Adamantan-1-yloxy)-2-hydroxyimino-3-oxo-butyric acid benzyl ester. A solution of 4-(Adamantan-1-yloxy)-3-oxo-butyric acid benzyl ester (4.2 g, 12.3 mmol) in THF (45 ml), acetic acid (50 ml) and water (4 ml) was stirred at 5° C. and a solution of sodium nitrite (1.65 g, 24 mmol) in water (10 ml) was added, slowly, dropwise. The mixture was allowed to warm to room temperature and stirred for 1 h. The solution was evaporated in vacuo and the residue was partitioned between ethyl acetate (100 ml) and water (100 ml) after adjusting the pH to 8 with saturated sodium bicarbonate. The organic phase was washed with brine (100 ml), dried (MgSO$_4$) and evaporated to afford the product as a white solid. (4.36 g, 95%). $^1$H NMR (CDCl$_3$) 10.00 (1H, br.s), 7.36 (5H, m), 5.35 (2H, s), 4.58 (2H, s), 2.14 (3H, br.s), 1.76–1.52 (12H, m).

Step d. 5-(Adamantan-1-yloxymethyl)-2-cyclohexyl-3-hydroxy-1H-imidazole-4-carboxylic acid benzyl ester. A solution of 4-(Adamantan-1-yloxy)-2-hydroxyimino-3-oxo-butyric acid benzyl ester (4.36 g, 11.79 mmol), ammonium acetate (18.33 g, 235 mmol) and cyclohexanecarboxaldehyde (1.7 ml, 17.1 mmol) in acetic acid (75 ml) was heated at 70° C. for 2 hr. The solution was evaporated in vacuo the residue was partitioned between ethyl acetate and saturated sodium bicarbonate (pH 8). The organic phase was washed with brine, dried (MgSO$_4$) and evaporated. The residue was purified by flash column chromatography on silica eluting with DCM/ethyl acetate (85:15) to afford the product. (3.17 g, 58%). $^1$H NMR (CDCl$_3$) 11.34 (1H, br s), 7.40 (5H, m), 5.37 (2H, s), 4.49 (2H, s), 2.89 (1H, m) 2.05 (3H, br s), 1.93–1.49 18H, m), 1.38–1.26 (4H, m).

Step e. 5-(Adamantan-1-yloxymethyl)-3-benzyloxy-2-cyclohexyl-1H-imidazole-4-carboxylic acid benzyl ester. To a solution of Adamantan-1-yloxymethyl)-2-cyclohexyl-3-hydroxy-1H-imidazole-4-carboxylic acid benzyl ester (1.3 g, 2.8 mmol), and potassium carbonate (0.41 g, 3 mmol) in DMF (50 ml) was added benzyl bromide (0.32 ml, 2.8 mmol) and the mixture stirred at room temperature for 16 hr. The reaction mixture was partitioned between ethyl acetate and 1M HCl. The organic phase was washed with 1M HCl, saturated sodium bicarbonate, brine, dried (MgSO$_4$), and evaporated. The residue was purified by flash column chromatography on silica, eluting with DCM/ethyl acetate (98:2) to afford the product, (1.38 g, 89%). $^1$H NMR (CDCl$_3$) 7.45 (2H, m), 7.38 (8H, m), 5.37 (2H, s), 5.30 (2H, s), 4.59 (2H, s), 2.66 (1H, m), 2.09 (2H, br.s), 1.81–1.52 (18H, m), 1.27 (4H, m).

Step f. 5-(Adamantan-1-yloxymethyl)-3-benzyloxy-2-cyclohexyl-1H-imidazole-4-carboxylic acid. A solution of 5-(Adamantan-1-yloxymethyl)-2-cyclohexyl-3-benzyloxy-1H-imidazole-4-carboxylic acid benzyl ester (1.37 g, 2.47 mmol) and potassium hydroxide (0.55 g, 9.9 mmol) in ethanol (20 ml) and water (2 ml) was refluxed for 1 hr. Most of the ethanol was evaporated and the residue was diluted with water (20 ml) and the solution acidified to pH 3 with 1M HCl. The product was extracted with DCM (2×30 ml). The combined organic phase was washed with brine, dried (MgSO$_4$), and evaporated. The residue was purified by flash column chromatography on silica, eluting with DCM/ethyl actetate (95:5) to afford the product, (0.89 g, 77%). $^1$H NMR (CDCl$_3$) 12.67 (1H, br.s), 7.42 (5H, m), 5.28 (2H, s), 4.79 (2H, s), 2.56 (1H, m), 2.23 (3H, br.s), 1.90 (6H, br.s), 1.78–1.62 (11H, m), 1.51 (2H, m) 1.23 (3H, m).

Step g. 5-(Adamantan-1-yloxymethyl)-3-benzyloxy-2-cyclohexyl-1H-imidazol-4-carboxylic acid hydrazide. The title compound was prepared essentially according to the procedure in Example 8, step a, with the modification that 5-(Adamantan-1-yloxymethyl)-3-benzyloxy-1H-2-cyclohexyl-imidazole-4-carboxylic acid was used instead of 5-(Adamantan-1-yloxymethyl)-2-cyclohexyl-1H-imidazole-4-carboxylic acid. $^1$H NMR (CDCl$_3$) 9.63 (1H, br s), 7.48 (2H, m), 7.41 (3H, m), 5.34 (2H, s), 4.58 (2H, s), 4.01 (2H, br.s), 2.60 (1H, m), 2.20 (3H, br s), 1.88 (6H, s), 1.79–1.53 (13H, m), 1.25 (3H, m).

Step h. 3-{N$^1$-[5-(Adamantan-1-yloxymethyl)-3-benzyloxy-2-cyclohexyl-1H-imidazole-4-carbonyl]-hydrazinocarbonyl}-benzoic acid methyl ester. The title compound was prepared essentially using the procedure in Example 8, step b, with the modification that 5-(Adamantan-1-yloxymethyl)-3-benzyloxy-2-cyclohexyl-1H-imidazole-4-carboxylic acid hydrazide. was used instead of 5-(Adamantan-1-yloxymethyl)-2-cyclohexyl-1H-imidazole-4-carboxylic acid hydrazide. $^1$H NMR (CDCl$_3$) 11.16 (1H, d), 9.21 (1H, br s), 8.51 (1H, s), 8.20 (1H, d), 8.12 (1H, d), 7.54 (1H, t), 7.46 (2H, m), 7.38 (3H, m), 5.33 (2H, s), 4.74 (2H, s), 3.94 (3H, s), 2.60 (1H, m), 2.17 (3H, br s), 1.90 (6H, s), 1.79 (2H, m), 1.62 (11H, m), 1.26 (3H, m).

Step i. 3-{5-[5-(Adamantan-1-yloxymethyl)-3-benzyloxy-2-cyclohexyl-1H-imidazol-4-yl]-[1,3,4]oxadiazol-2-yl}-benzoic acid methyl ester. The title compound was prepared essentially using the procedure in Example 9, step a, with the modification that 3-{N$^1$-[5-(Adamantan-1-yloxymethyl)-3-benzyloxy-2-cyclohexyl-1H-imidazole-4-carbonyl]-hydrazinocarbonyl}-benzoic acid methyl ester was used instead of 3-{N$^1$-[5-(Adamantan-1-yloxymethyl)-2-cyclohexyl-1H-imidazole-4-carbonyl]-hydrazinocarbonyl}-benzoic acid methyl ester. $^1$H NMR (CDCl$_3$) 8.77 (1H, s), 8.33 (1H, d), 8.24 (1H, d), 7.63 (1H, t), 7.53 (2H, m), 7.45 (3H, m), 5.37 (2H, s), 4.77 (2H, s), 3.97 (3H, s), 2.73 (1H, m), 2.14 (3H, br s), 1.87–1.56 (19H, m), 1.27 (3H, m).

Step j. 3-{5-[5-(Adamantan-1-yloxymethyl)-3-benzyloxy-2-cyclohexyl-1H-imidazol-4-yl]-[1,3,4]oxadiazol-2-yl}-benzoic acid. A solution of 3-{5-[5-(Adamantan-1-yloxymethyl)-3-benzyloxy-2-cyclohexyl-1H-imidazol-4-yl]-[1,3,4]oxadiazol-2-yl}-benzoic acid methyl ester, (0.61 g, 0.98 mmol) and lithium hydroxide hydrate (0.16 g, 3.92 mmol) in THF/water 1:1 (15 ml) was stirred at room temperature for 16 hr. The THF was evaporated and the residue diluted with water (20 ml) and the solution acidified to pH 3 with 1M HCl. And extracted with DCM (2×20 ml). The combined organic phase was washed with brine (20 ml), and evaporated to afford the product, (0.534 g, 90%). $^1$H NMR (D$_6$ DMSO) 13.40 (1H, br s), 8.57 (1H, s), 8.30 (1H, d), 8.19 (1H, d), 7.76 (1H, t), 7.50 (2H, m), 7.47 (3H, m), 5.36 (2H, s), 4.60 (2H, s), 2.66 (1H, m), 2.07 (3H, br.s), 1.75–1.17 (22H, m).

Step k. 3-{5-[5-(Adamantan-1-yloxymethyl)-2-cyclohexyl-3-hydroxy-1H-imidazol-4-yl]-[1,3,4]oxadiazol-2-yl}-benzoic acid. A solution of 3-{5-[5-(Adamantan-1-yloxymethyl)-3-benzyloxy-2-cyclohexyl-1H-imidazol-4-yl]-[1,3,4]oxadiazol-2-yl}-benzoic acid (0.53 g, 0.878 mmol) in THF/methanol 1:1 (20 ml) was hydrogenated over 10% palladium on carbon catalyst for 1.5 hr. The catalyst was removed by filtration and the filtrate evaporated to afford the product, (0.419 g, 92%) $^1$H NMR (D$_6$ DMSO) 13.40 (1H, br s), 12.10 (1H, s), 8.57 (1H, s), 8.32 (1H, d), 8.18 (1H, d), 7.76 (1H, t), 4.55 (2H, s), 2.86 (1H, m), 2.06 (3H, br s), 1.90–1.49 (19H, m), 1.41–1.22 (3H, m). The acid was converted to the N-methyl-D-glucamine salt and lyophilised from water/dioxan. Found: C, 58.27; H, 7.46; N, 9.34%. C$_{26}$H$_{51}$N$_5$O$_{10}$.1.5H$_2$O Requires: C, 58.32; H, 7.35; N, 9.45%.

EXAMPLE 18

Reaction Scheme 9

3-{3-[5-(Adamantan-1-yloxymethyl)-2-cyclohexyl-1H-imidazol-4-yl]-[1,2,4]oxadiazol-5-yl}-benzoic acid Step a. 5-(Adamantan-1-yloxymethyl)-2-cyclohexyl-1H-imidazole-4-carbonitrile. Oxalyl chloride (583 μl, 6.68 mmol) and 2 drops of DMF were added to a suspension of 5-(adamantan-1-yloxymethyl)-2-cyclohexyl-1H-imidazole-4-carboxylic acid (1.60 g, 4.46 mmol) in DCM (20 ml) and stirred at room temperature for 1 hour, to give a solution. The solvent and excess oxalyl chloride were removed by evaporation, the residue was suspended in THF (30 ml) and ammonia was bubbled through for 10 minutes. The mixture was stirred at room temperature for 1.5 hours then diluted with ethyl acetate (60 ml), washed with water (2×30 ml) and the organic layer was dried over anhydrous magnesium sulfate. The solvent was evaporated to give a foam (1.64 g).

Thionyl chloride (407 μl, 5.58 mmol) was added to DMF (8 ml) at −10° C. and the mixture was stirred at −10° C. for 10 minutes. The crude 5-(adamantan-1-yloxymethyl)-2-cyclohexyl-1H-imidazole-4-carboxylic amide (1.33 g, assume 3.72 mmol) was added in four portions over a period of 20 minutes. The mixture was allowed to reach room temperature slowly and stirred, under argon, for 18 hours. The mixture was diluted with DCM (100 ml) and washed with water (3×50 ml). The organic layer was dried over anhydrous magnesium sulfate and the solvent evaporated to give a brown oil. The crude product was purified by flash column chromatography (Silica, DCM/methanol 98:2). Yield 878 mg (70% over two steps). $^1$H NMR (300 MHz, CDCl3): 9.55 (1H, br), 4.62 (2H, s), 2.66 (1H, m), 2.20 (3H, br s), 1.98 (2H, m), 1.85–1.59 (15H, m), 1.49–1.30 (5H, m).

Step b. 5-(Adamantan-1-yloxymethyl)-2-cyclohexyl-N-hydroxy-1H-imidazole-4-carboxamidine. A solution of 5-(adamantan-1-yloxymethyl)-2-cyclohexyl-1H-imidazole carbonitrile (1.03 g, 3.03 mmol), hydroxylamine hydrochloride (464 mg, 6.68 mmol) and triethylamine (973 μl, 6.98 mmol) in ethanol (10 ml) was refluxed, under argon, for 7 hours. The reaction mixture was diluted with water (40 ml), neutralised (to pH 7) with 2M hydrochloric acid, then was extracted with DCM (3×40 ml). The combined organic extracts were dried over anhydrous magnesium sulfate and the solvent evaporated to give the product as a yellow solid. Yield 1.13 g (100%).

$^1$H NMR (300 MHz, CDCl3): 9.75–9.25 (1H, br), 6.10 (1H, br), 5.35 (1H, br), 4.69 (2H, s), 2.64 (1H, m), 2.16 (3H, br s), 1.97 (2H, m), 1.71 (8H, br s), 1.68–1.50 (7H, m), 1.46–1.22 (5H, m).

Step c. 3-{3-[5-(Adamantan-1-yloxymethyl)-2-cyclohexyl-1H-imidazol-4-yl]-[1,2,4]oxadiazol-5-yl}-benzoic acid methyl ester. CDI (541 mg, 3.34 mmol) was added to a solution of isophthalic acid, monomethyl ester (547 mg, 3.03 mmol) in DMF (10 ml) and stirred for 30 minutes. 5-(Adamantan-1-yloxymethyl)-2-cyclohexyl-N-hydroxy-1H-imidazole-4-carboxamidine (1.13 g, 3.03 mmol) was added and the mixture was stirred at room temperature, under argon, for 6 hours. The reaction mixture was diluted with ethyl acetate (50 ml) and washed with saturated sodium chloride solution (3×25 ml). The organic layer was dried over anhydrous magnesium sulfate and the solvent evaporated to give a gum. This was purified by flash chromatography (Silica, DCM/methanol 97:3). yielding 1.00 g (62%) of product which was dissolved in diglyme and the solution heated to 110° C., under argon, for 19 hours. The mixture was diluted with ethyl acetate (30 ml) and washed with water (3×15 ml). The organic layer was dried over anhydrous magnesium sulfate and the solvent evaporated to give a brown oil. The crude product was purified by flash chromatography (Silica, ethyl acetate/hexane 7:3). Yield 177 mg (92%). $^1$H NMR (300 MHz, CDCl$_3$): 9.35 & 9.20 (1H, 2xbr s), 8.94 & 8.85 (1H, 2xs), 8.43 & 8.35 (1H, 2xd, J=7.8 Hz), 8.26 (1H, d, J=7.8 Hz), 7.63 (1H, t, J=7.8 Hz), 4.97 & 4.86 (2H, 2xs), 4.00 & 3.98 (3H, 2xs), 2.85 (1H, m), 2.20–2.11 (5H, m), 1.98–1.26 (20H, m).

Step d. 3-{3-[5-(Adamantan-1-yloxymethyl)-2-cyclohexyl-1H-imidazol-4-yl]-[1,2,4]oxadiazol-5-yl}-benzoic acid. A suspension of 3-{3-[5-(adamantan-1-yloxymethyl)-2-cyclohexyl-1H-imidazol-4-yl]-[1,2,4]oxadiazol-5-yl}-benzoic acid methyl ester (463 mg, 0.90 mmol) in 1:1 ethanol/water (6 ml) was refluxed with potassium hydroxide (201 mg, 3.58 mmol) for 1 hour. The ethanol was evaporated under reduced pressure and water (10 ml) was added to the residue. It was neutralised (to pH 7) with 2M hydrochloric acid and the resultant precipitate was recovered by filtration, dried under vacuum at 60° C. and triturated with ether to give a pink solid. Yield 312 mg (69%).

$^1$H NMR (300 MHz, d$_6$-DMSO): 12.50 (1H, br), 12.25 (1H, br s), 8.69 (1H, s), 8.33 (1H, d, J=7.5 Hz), 8.22 (1H, d, J=7.8 Hz), 7.76 (1H, t, J=7.7 Hz), 4.84 (2H, s), 2.69 (1H, m), 2.12 (3H, br s), 1.94–1.90 (2H, m), 1.80–1.49 (17H, m), 1.35–1.21 (3H, m).

The acid was converted to the N-methyl-D-glucamine salt and lyophilised from water/dioxan. Found: C, 59.02; H, 7.46; N, 9.57%; C$_{36}$H$_{51}$N$_5$O$_9$.2H$_2$O requires: C, 58.92; H, 7.55; N, 9.54%.

EXAMPLE 19

2-{2-[5-(Adamantan-1-yloxymethyl)-2-cyclohexyl-1H-imidazol-4-yl]-thiazol-4-yl}-benzoic acid This was prepared essentially as in Example 6 except that methyl 2-(2-bromoacetyl)benzoate was used in step d in place of the meta-substituted isomer. $^1$H NMR (300 MHz, d$_6$-DMSO) 12.70 (2H, br s), 7.67 (3H, m), 7.57 (1H, t), 7.47 (1H, t), 4.81 (2H, s), 2.84 (1H, m), 2.05 (3H, br s), 1.92 (2H, m), 1.82–1.55 (16H, m), 1.31 (4H, m). The acid was converted to the N-methyl-D-glucamine salt and lyophilized from water/dioxan. Found: C, 58.06; H, 7.78; N, 7.43%. C$_{37}$H$_{52}$N$_4$O$_8$S.3H$_2$O requires C, 57.98; H, 7.62; N, 7.31%.

The compounds of the examples were tested for gastrin (CCK$_2$) antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing 3×10$^{-8}$ M 5-methylfurmethide, maintained at 37° and gassed vigorously with 95% O$_2$/5% CO$_2$. The stomach was continuously perfused at a rate of 1 ml min$^{-1}$ with unbuffered solution gassed with 100% O$_2$ with perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et al., Br. J. Pharmacol., 1985, 86, 581.

The results obtained at gastrin (CCK$_2$) receptors are set out in Table 1.

TABLE 1

| Example No. | Rat stomach pK$_B$ |
|---|---|
| 1 | 8.10 |
| 2 | 7.74 |
| 3 | 8.66 |
| 4 | 8.16 |
| 5 | 5.76 |
| 6 | 8.57 |
| 7 | 7.01 |
| 8 | 8.43 |
| 9 | 8.61 |
| 10 | 8.28 |
| 11 | 6.72 |
| 13 | 7.64 |
| 14 | 5.98 |
| 16 | 8.72 |
| 17 | 6.90 |
| 18 | 8.62 |

The compounds of certain examples were also tested in a CCK$_1$ binding assay as follows:

The pancreatata were removed from male guinea-pigs (200–300 g; Dunkin Hartley) and placed in ice-cold HEPES buffer (pH 7.2@21±3° C.). The pancreatata were homogenised in 40 ml ice-cold HEPES buffer using a polytron (Brinkmann, PT10, setting 10) 4×1 second. The homogenate was centrifuged at 39,800 g for 15 min at 4° C. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original wet weight), and filtered through a 500 μm pore-size Nytex mesh.

The membranes (400 μl; containing 0.375 μM PD134, 308) were incubated for 150 minutes at 21±3° C. in a final volume of 0.5 ml with HEPES buffer containing [$^{125}$I]-CCK$_8$ (S) (50 μl; 200 pM) and competing compound. Total and non-specific binding of [$^{125}$I]-CCK$_8$ (S) were defined using 50 μl of buffer and 50μ of 100 nM L-364,718 respectively. The assay was terminated by rapid filtration through pre-soaked Whatman GF/B filters using a Brandell Cell Harvetser. The filters were washed (3×3 ml) with ice-cold 50 mM Tris HCl (pH 7.4@4° C.) and bound radioactivity was determined by counting (1 min) in a gamma counter.

The results obtained at CCK$_1$ receptors are set out in Table 2.

| Example No. | Guinea-Pig Pancreas CCK$_1$ pK$_i$ |
|---|---|
| 1 | 6.13 |
| 2 | 5.93 |
| 3 | 6.37 |
| 4 | 6.47 |
| 5 | 6.40 |
| 6 | 5.94 |
| 7 | 6.57 |
| 8 | 6.87 |
| 9 | 6.26 |
| 10 | 6.41 |
| 12 | 5.67 |
| 13 | 5.49 |
| 14 | 5.01 |
| 16 | 6.33 |
| 17 | 5.23 |
| 18 | 6.30 |

It is found that the compositions and products of the present invention comprising a compound of formula (I) and a proton pump inhibitor reduce hyperplasia, associated with administration of proton pump inhibitors. This was measured according to the following experimental protocal.

Animals and Treatment:

40 male SPF Wistar rats (200 g) were divided into 4 treatment groups and 2 strata. The treatment of the 20 rats in a second stratum started 2 weeks after the treatment of the first stratum. The design of the study was completely randomised double blind with individual blinding; all rats were placed in a separate cage. Animals had continuous access to water and food.

Animals were treated once daily during 14 days:

Control group: 1 ml gastrin test drug vehicle+1 ml p.o. (gavage) 0.25% Methocel (Dow Corning)

PPI group: 1 ml gastrin test drug vehicle+1 ml p.o. (gavage) 25 mg/kg Rabeprazole in 0.25% Methocel.

GRA group: 1 ml gastrin test drug+1 ml p.o. (gavage) 0,25% Methocel

GRA-PPI group: 1 ml gastrin test drug+1 ml p.o.(gavage) 25 mg/kg Rabeprazole in 0.25% Methocel.

Gastrin test drug made up to an appropriate dose in physiologically compatible solvent.

Preparation of Tissue:

After removal of the fundus, the stomach were rinsed with phosphate buffered saline prior to fixation with 4% formalin in Millonig buffer. After 4 hours immersion in fixative solutions at room temperature, tissue was rinsed in phosphate buffered saline (PBS), dehydrated and embedded in paraffin using the Leitz paraffin embedding station (Leitz TP 1050; Germany) dehydration module and paraffin embedding module (Leitz EG 1160; Germany).

Cross sections (3 μm thick) of the oxyntic part of the stomach were made at 3 levels, each separated by a distance of 400 μm.

Immunostaining

The following indirect immunofluorescence labeling method was used:
- removal of paraffin and rehydratation of the sections followed by a blocking step
- primary antibodies: polyclonal guinea pig anti-histidine decarboxylase, 1/2000 (from Euro-Diagnostica) and monoclonal mouse anti PCNA 1/2500 (Clone PC10 from Sigma). All antibodies were diluted in a 0.2% BSA solution. Sections were incubated overnight at 4° C. and then washed with a BSA solution.
- secondary antibodies: goat anti guinea pig coupled to CY5, 1/500 (from Jackson Laboratories) and goat anti-mouse coupled to Cy3, 1/250 (from Jackson Laboratories); incubation for 4 hours at 37° C. After rinsing with BSA and PBS solutions, sections were mounted with slowfade (Molecular Probes Europe BV), and stored at 4° C.

Imaging

Fluorescence labelling was observed with an epifluorescence microscope or a Zeiss LSM510 (Carl Zeiss Jena GmbH) confocal microscope.

By using CY5- and CY3-coupled antibodies, the high autofluorescence properties of the oxyntic mucosa were circumvented when sections are illuminated by a 488 nm (FITC channel) light source. Negative controls, by omitting the primary antibodies, and an isotype control staining for PCNA showed complete absence of staining. The specific labelling of PCNA was checked using double staining with TOPRO-3® (Molecular Probes Europe BV), a nuclear stain. Only in the most luminal located epithelial cells, non-specific cytoplasmic labelling was present. In the glandular part of the mucosa, non-specific PCNA-staining was absent.

For determination of the labelling index of ECL cells, at least 80 confocal images per rat were taken from the 3 slides at the 3 different levels. The ratio of double labelled cells (HDC+PCNA) and all HDC labelled cells yielded the labelling index of ECL cells.

Proliferation activity of ECL cells in the PPI group is expected to be increased compared with sham, GRA and GRA-PPI groups (Eissele, R., Patberg, H., Koop, H., Krack, W., Lorenz, W., McKnight, A. T., and Arnold, R. Effect of gastrin receptor blockade on endrocine cells in rats during achlorhydria. *Gastroenterology*, 103, 1596–1601, 1992). Increased proliferation by PPI will be completely blocked by GRA.

What is claimed is:

1. A compound of formula (I)

$$R^1 \underset{Y}{\overset{X}{\diagdown}} \underset{Z-Q}{\overset{(CR^2R^3)_n-R^4}{\diagup}} \quad (I)$$

wherein
n is from 1 to 3,
X and Y are independently =N— or —N($R^5$)— wherein $R^5$ is selected from the group consisting of H, Me, Et, Pr, Bn, —OH and —$CH_2COOR^6$, wherein $R^6$ represents H, Me, Et, Pr or Bn;
$R^1$ is H or a $C_1$–$C_{15}$ saturated carbocyclic ring optionally substituted with OMe, $NMe_2$, $CF_3$, Me, F, Cl, Br or I wherein up to three H atoms may optionally be replaced by halogen atoms;
$R^2$ is selected from H, Me, Et, Pr and OH, each $R^2$ being independently selected from H, Me, Et, Pr and OH when n is greater than 1;
$R^3$ is selected from the group consisting of H, Me, Et and Pr when n is 1; or, when n is greater than 1, each $R^3$ is independently selected from the group consisting of H, Me, Et and Pr, or two $R^3$ groups on neighbouring carbon atoms are linked to form a $C_3$ to $C_6$ carbocyclic ring, or two $R^3$ groups are absent from neighbouring carbon atoms which are linked by a double bond; or $R^2$ and $R^3$ on the same carbon atom together represent an =O group;
$R^4$ is H or a $C_3$ to $C_{10}$ alicyclic ring wherein up to three H atoms may optionally be replaced by halogen atoms;
Z is selected from the group consisting of:

[structures: oxadiazole, imidazole, oxadiazole, oxazole, triazole, thiadiazole or thiazole]

Q is a 6-membered aromatic carbocycle substituted with 1 or 2 V groups and optionally substituted with 1, 2 or 3 T groups;
V is selected from the group consisting of —CO—NH—$SO_2$—Ph, —$SO_2$—NH—CO—Ph, —$CH_2OH$, or a group of the formula —$R^7U$, wherein U is selected from the group consisting of —COOH, tetrazolyl, —CONHOH and —$SO_3H$; and $R^7$ is selected from the group consisting of a bond; $C_1$ to $C_6$ hydrocarbylene, optionally substituted by hydroxy, amino or acetamido; —O—($C_1$ to $C_3$ alkylene)-; —$SO_2NR^8$—$CHR^9$—; —CO—$NR^8$—$CHR^9$—, wherein $R^8$ and $R^9$ are independently selected from H and methyl; and —NH—(CO)$_c$—$CH_2$—, wherein c is 0 or 1.

2. A compound according to claim 1 wherein X is =N and Y is —NH— or —N(OH)—.

3. A compound according to claim 1 wherein $R^1$ is $C_3$ to $C_{10}$ alicyclic.

4. A compound according to claim 1 wherein $R^1$ is cyclohexyl, bicyclo[2.2.2]oct-1-yl or tol-2-yl.

5. A compound according to claim 1, wherein $R^4$ is adamantyl, cycloheptyl, or cyclohexyl.

6. A compound according to claim 1, wherein $R^{12}$ is $C_3$ to $C_{12}$ carbocylic.

7. A compound according to claim 6 wherein $R^{12}$ is adamantyl, cycloheptyl, cyclohexyl or phenyl.

8. A compound according to claim 1, wherein $R^2$ and $R^3$ are H, and n is from 1 to 3.

9. A compound according to claim 1, wherein Z is

[structures]

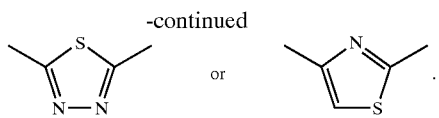

10. A compound according to claim 1, wherein Q is 3-carboxyphenyl.

11. A compound which is degraded in vivo to yield a compound according to claim 1.

12. A method of making a compound according to claim 1 wherein (i) X is NH
(ii) Y is =N or —N(OH) and
(iii) Z is the 2,5-diradical derived from [1,3,4]oxadiazole (furazan) or [1,3,4]thiadiazole said method comprising the steps of coupling a compound of formula (III) or (XIX), or a suitably protected derivative thereof,

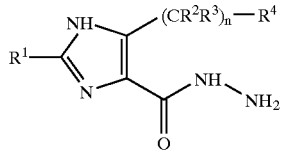 (III)

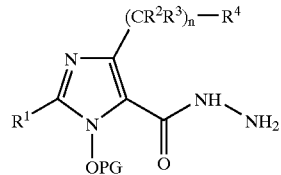 (XIX)

with a monoester of isophthalic acid, and cyclising the resultant coupled product with $Ph_3P/CCl_4/DBU$, when Z is the 2,5-diradical derived from [1,3,4]oxadiazole (furazan) or with Lawesson's reagent when Z is the 2,5-diradical derived from [1,3,4]thiadiazole.

13. A pharmaceutical composition comprising a compound according to claim 1 together with a pharmaceutically acceptable diluent or carrier.

14. A method of treating or alleviating the symptoms of a gastrointestinal disorder, comprising administering to a patient suffering from said disorder a therapeutically beneficial amount of a composition according to claim 13.

* * * * *